United States Patent
McPherson et al.

(10) Patent No.: US 11,243,217 B2
(45) Date of Patent: Feb. 8, 2022

(54) MANAGEMENT OF ACUTE KIDNEY INJURY USING INSULIN-LIKE GROWTH FACTOR-BINDING PROTEIN 7 AND TISSUE INHIBITOR OF METALLOPROTEINASE 2

(71) Applicants: ASTUTE MEDICAL, INC., San Diego, CA (US); UNIVERSITY OF PITTSBURGH—OF THE COMMONWEALTH SYSTEM OF HIGHER EDUCATION, Pittsburgh, PA (US)

(72) Inventors: Paul McPherson, Encinitas, CA (US); James Patrick Kampf, San Diego, CA (US); John A. Kellum, Pittsburgh, PA (US)

(73) Assignees: Astute Medical, Inc., San Diego, CA (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/307,366

(22) PCT Filed: Jun. 6, 2017

(86) PCT No.: PCT/US2017/036227
§ 371 (c)(1),
(2) Date: Dec. 5, 2018

(87) PCT Pub. No.: WO2017/214203
PCT Pub. Date: Dec. 14, 2017

(65) Prior Publication Data
US 2019/0302131 A1    Oct. 3, 2019

Related U.S. Application Data

(60) Provisional application No. 62/346,381, filed on Jun. 6, 2016.

(51) Int. Cl.
*G01N 33/74* (2006.01)
*G01N 33/493* (2006.01)
*G01N 33/68* (2006.01)

(52) U.S. Cl.
CPC ........... *G01N 33/74* (2013.01); *G01N 33/493* (2013.01); *G01N 33/68* (2013.01); *G01N 2800/347* (2013.01)

(58) Field of Classification Search
CPC ...... G01N 33/74; G01N 33/493; G01N 33/68; G01N 2800/347
See application file for complete search history.

(56) References Cited

U.S. PATENT DOCUMENTS

| | | | |
|---|---|---|---|
| 5,118,614 A | 6/1992 | Rybák et al. | |
| 5,324,634 A | 6/1994 | Zucker | |
| 5,480,792 A | 1/1996 | Buechler et al. | |
| 5,525,524 A | 6/1996 | Buechler et al. | |
| 5,571,698 A | 11/1996 | Ladner et al. | |
| 5,631,171 A | 5/1997 | Sandstrom et al. | |
| 5,679,526 A | 10/1997 | Buechler et al. | |
| 5,824,799 A | 10/1998 | Buechler et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,019,944 A | 2/2000 | Buechler | |
| 6,057,098 A | 5/2000 | Buechler et al. | |
| 6,113,855 A | 9/2000 | Buechler | |
| 6,140,045 A | 10/2000 | Wohlstadter et al. | |
| 6,143,576 A | 11/2000 | Buchler | |
| 6,218,122 B1 | 4/2001 | Friend et al. | |
| 6,664,385 B1 | 12/2003 | Sanicola-Nadel et al. | |
| 6,784,154 B2 | 8/2004 | Westenfelder | |
| 6,861,404 B1 | 3/2005 | Cohen et al. | |
| 6,941,172 B2 | 9/2005 | Nachum | |
| 7,138,230 B2 | 11/2006 | Hu et al. | |
| 7,141,382 B1 | 11/2006 | Parikh et al. | |
| 7,235,358 B2 | 6/2007 | Wohlgemuth et al. | |
| 7,608,413 B1 | 10/2009 | Joseloff et al. | |

(Continued)

FOREIGN PATENT DOCUMENTS

| | | |
|---|---|---|
| CN | 1791797 | 6/2006 |
| EP | 0828159 | 3/1998 |

(Continued)

OTHER PUBLICATIONS

Kashani et al. Discovery and validation of cell cycle arrest biomarkers in human acute kidney injury. Critical Care, 2013; 17:R25 (Year: 2013).*
Kashani et al. Critical Care, 2013; 17:R25 (Year: 2013).*
Abd El Latif et al., "Urinary Epidermal Growth Factor Excretion: A Useful Prognostic Marker for Progression of Renal Damage in Children," J Med Sci, Oct. 1, 2007, 7(7):1171-1176.
Abou-Shousha et al., "Interleukin-2 Regulatory Effect on P-Selectin and lnterleukin-8 Production in Patients with Chronic Renal Failure," Egypt J Immunol, 2006, 13(1):11-18.
Akcay et al., "Mediators of Inflammation in Acute Kidney Injury," Mediators Inflamm, 2009, 2009:137072 (12 pp).
Albright, "Acute Renal Failure: A Practical Update," Mayo Clin Proc, Jan. 2001, 76(1):67-74.

(Continued)

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

The present invention provides methods and compositions for identifying patients at risk of kidney injury. A risk score, which is a composite of a urinary concentration of IGFBP7 (insulin-like growth factor-binding protein 7) and a urinary concentration of TIMP-2 (tissue inhibitor of metalloproteinase 2), is determined obtained from the patient, and is used to manage patient treatment.

5 Claims, 1 Drawing Sheet

(56) References Cited

U.S. PATENT DOCUMENTS

| | | |
|---|---|---|
| 7,623,910 B2 | 11/2009 | Couderc et al. |
| 7,662,578 B2 | 2/2010 | Devarajan |
| 7,833,699 B2 | 11/2010 | Locht et al. |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 8,778,615 B2 | 7/2014 | Anderberg et al. |
| 8,993,250 B2 | 3/2015 | Anderberg et al. |
| 9,029,093 B2 | 5/2015 | Anderberg et al. |
| 9,057,735 B2 | 6/2015 | Anderberg et al. |
| 9,229,010 B2 | 1/2016 | Anderberg et al. |
| 9,360,488 B2 | 6/2016 | Anderberg et al. |
| 9,459,261 B2 | 10/2016 | Anderberg et al. |
| 9,696,322 B2 | 7/2017 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | McPherson et al. |
| 2002/0012906 A1 | 1/2002 | Comper |
| 2002/0055627 A1 | 5/2002 | Rosen et al. |
| 2003/0003588 A1 | 1/2003 | Comper |
| 2003/0186308 A1 | 10/2003 | Young et al. |
| 2004/0053309 A1 | 3/2004 | Holt et al. |
| 2004/0106155 A1 | 6/2004 | Comper |
| 2004/0126767 A1 | 7/2004 | Anderberg et al. |
| 2004/0253637 A1 | 12/2004 | Buechler et al. |
| 2005/0002934 A1 | 1/2005 | Reed |
| 2005/0048033 A1 | 3/2005 | Fraser et al. |
| 2005/0084880 A1 | 4/2005 | Duman et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2006/0257903 A1 | 11/2006 | Akil et al. |
| 2007/0031905 A1 | 2/2007 | Shariat |
| 2007/0087387 A1 | 4/2007 | Devarajan |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0184439 A1 | 8/2007 | Guilford et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0090759 A1 | 4/2008 | Kokenyesi et al. |
| 2008/0133141 A1 | 6/2008 | Frost |
| 2008/0153092 A1 | 6/2008 | Kienle et al. |
| 2008/0166717 A1 | 7/2008 | Thorin |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0004687 A1 | 1/2009 | Mansfield et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0130693 A1 | 5/2009 | Bassi et al. |
| 2009/0148539 A1 | 6/2009 | Elias et al. |
| 2009/0176656 A1 | 7/2009 | Halloran |
| 2009/0179287 A1 | 7/2009 | Inaba |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2010/0267061 A1 | 10/2010 | Hsieh et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0156701 A1 | 6/2012 | Anderberg et al. |
| 2012/0190044 A1 | 7/2012 | Anderberg et al. |
| 2012/0190051 A1 | 7/2012 | Anderberg et al. |
| 2012/0208717 A1 | 8/2012 | Hu et al. |
| 2012/0283128 A1 | 11/2012 | Anderberg et al. |
| 2012/0329071 A1 | 12/2012 | Chance et al. |
| 2013/0035290 A1 | 2/2013 | Elias et al. |
| 2013/0157881 A1 | 6/2013 | Anderberg et al. |
| 2013/0210043 A1 | 8/2013 | Anderberg et al. |
| 2014/0213477 A1 | 7/2014 | Anderberg et al. |
| 2014/0315734 A1 | 10/2014 | Arnold et al. |
| 2014/0323594 A1 | 10/2014 | Anderberg et al. |
| 2014/0343600 A1 | 11/2014 | Leschinsky |
| 2014/0377777 A1 | 12/2014 | Anderberg et al. |
| 2016/0146832 A1 | 5/2016 | Chawla et al. |
| 2017/0248613 A1 | 8/2017 | Anderberg et al. |
| 2018/0074054 A1 | 3/2018 | McPherson et al. |
| 2019/0263926 A1 | 8/2019 | McPherson et al. |

FOREIGN PATENT DOCUMENTS

| | | |
|---|---|---|
| EP | 1777523 | 4/2007 |
| EP | 1905846 | 4/2008 |
| EP | 2261660 | 12/2010 |
| JP | 2003-081838 | 3/2003 |
| RU | 2180965 | 3/2002 |
| SU | 1429031 | 10/1988 |
| WO | WO 1998/055508 | 12/1998 |
| WO | WO 2003/054004 | 7/2003 |
| WO | WO 2003/075016 | 9/2003 |
| WO | WO 2004/005934 | 1/2004 |
| WO | WO 2004/059293 | 7/2004 |
| WO | WO 2005/087264 | 9/2005 |
| WO | WO 2006/010529 | 2/2006 |
| WO | WO 2006/072654 | 7/2006 |
| WO | WO 2006/083986 | 8/2006 |
| WO | WO 2007/013919 | 2/2007 |
| WO | WO 2007/041623 | 4/2007 |
| WO | WO 2007/082586 | 7/2007 |
| WO | WO 2007/124331 | 11/2007 |
| WO | WO 2007/124419 | 11/2007 |
| WO | WO 2008/060607 | 5/2008 |
| WO | WO 2008/067065 | 6/2008 |
| WO | WO 2008/084331 | 7/2008 |
| WO | WO 2008/089994 | 7/2008 |
| WO | WO 2008/104804 | 9/2008 |
| WO | WO 2008/116867 | 10/2008 |
| WO | WO 2008/122670 | 10/2008 |
| WO | WO 2008/154238 | 12/2008 |
| WO | WO 2009/038742 | 3/2009 |
| WO | WO 2009/062520 | 5/2009 |
| WO | WO 2010/025424 | 3/2010 |
| WO | WO 2010/025434 | 3/2010 |
| WO | WO 2010/045714 | 4/2010 |
| WO | WO 2010/048346 | 4/2010 |
| WO | WO 2010/048347 | 4/2010 |
| WO | WO 2010/054389 | 5/2010 |
| WO | WO 2010/091236 | 8/2010 |
| WO | WO 2010/111746 | 10/2010 |
| WO | WO 2010/128158 | 11/2010 |

(56) References Cited

FOREIGN PATENT DOCUMENTS

| | | |
|---|---|---|
| WO | WO 2011/017614 | 2/2011 |
| WO | WO 2011/025917 | 3/2011 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/070935 | 5/2014 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/060525 | 4/2017 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Altom et al. "Optimizing enzyme-linked immunosorbent assays on automated 96-well plate robotic systems" Laboratory Robotics and Automation, vol. 2, Issue: 3, pp. 139-146, Journal, 1990, CODEN:LRAUEY, ISSN: 0895-7533.
Amemiya et al., "Insulin like growth factor binding protein-7 reduces growth of human breast cancer cells and xenografted tumors," Breast Cancer Res Treat, May 2010 (pub online), 126:373-384.
Anders et al., "Chemokines and chemokine receptors are involved in the resolution or progression of renal disease," Kidney Int, Feb. 2003, 63(2):401-415.
Anilkumar et al., "Trimeric assembly of the C-terminal region of Thrombospondin-1 or Thrombospondin-2 is necessary for cell spreading and fascin spike organization," J Cell Sci, Jun. 2002, 115(Pt 11):2357-2366.
Aregger et al., "Identification of IGFBP-7 by urinary proteomics as a novel prognostic marker in early acute kidney injury," Kidney International, Sep. 2013 (pub online), 85(4):909-919.
Arribas et al., "ADAM17 as a Therapeutic Target in Multiple Diseases," Curr Pharm Des, 2009, 15(20):2319-2335.
Arrizabalaga et al., "Tubular and Interstitial Expression of ICAM-1 as a Marker of Renal Injury in IgA Nephropathy," Am J Nephrol, Jan. 2003 (Epub), 23(3):121-128.
Bagshaw et al., "A multi-centre evaluation of the RIFLE criteria for early acute kidney injury in critically ill patients," Nephrol Dial Transplant, Oct. 2007 (advance access pub), 23(4):1203-1210.
Bagshaw et al., "Urinary biomarkers in septic acute kidney injury," Intensive Care Med, May 2007 (Epub), 33(7):1285-1296.
Bajwa et al., "Immune Mechanisms and Novel Pharmacological Therapies of Acute Kidney Injury," Curr Drug Targets, Dec. 2009, 10(12):1196-1204.
Barrera-Chimal et al., "Hsp72 is an early and sensitive biomarker to detect acute kidney injury," EMBO Mol Med, Dec. 2010 (Epub), 3(1):5-20.
Basile et al., "Renal ischemia reperfusion inhibits VEGF expression and induces ADAMTS-1, a novel VEGF inhibitor," Am J Physiol Renal Physiol, Feb. 6, 2008, 294(4):F928-F936.
Basu et al. "Identification of candidate serum biomarkers for severe septic shock-associated kidney injury via microarray," Grit Care, Nov. 2011 (Epub);15(6):R273. doi: 10.1186/cc10554.
Bellomo et al., "Acute renal failure—definition, outcome measures, animal models, fluid therapy and information technology needs: the Second International Consensus Conference of the Acute Dialysis Quality Initiative (ADQI) Group," Grit Care, May 2004 (Epub), 8(4):R204-R212.

Bennett et al., "Chronic cyclosporine nephropathy: The Achilles' heel of immunosuppressive therapy," Kidney Int., 1996, 50(4):1089-1100.
Berahovich et al., "Proteolytic Activation of Alternative CCR1 Ligands in Inflammation," J Immunol, Jun. 2005, 174(11):7341-7351.
Beushausen, "NWG Biomarker Objectives," ILSI Health and Environmental Sciences Institute, ILSI-HESI Annual Meeting, 2006, 17 pp.
Bicik et al., "Role of Transforming Growth Factor-beta2 in, and a Possible Transforming Growth Factor-beta2 Gene Polymorphism as a Marker of, Renal Dysfunction in Essential Hypertension: A Study in Turkish Patients," Current Therapeutic Research, Jul./Aug. 2005, 66(4):266-278.
Bihorac et al., "Validation of Cell-Cycle Arrest Biomarkers for Acute Kidney Injury Using Clinical Adjudication," Am J Respir Grit Care Med., Feb. 2014 (originally published), 189(8):932-939. doi: 10.1164/rccm.201401-00770C.
Biotrin International, "Biotrin Biomarkers: How late do you want to detect preclinical kidney damage?," Biotrin's acute kidney injury test (AKI Test), Biotrin's Preclinical Kidney Biomarkers, 8 pp.
Bone et al., "Definitions for Sepsis and Organ Failure and Guidelines for the Use of Innovative Therapies in Sepsis," American College of Chest Physicians/Society of Critical Care Medicine, Jun. 1992, 101(6):1644-55.
Bonomini et al., "Serum Levels of Soluble Adhesion Molecules in Chronic Renal Failure and Dialysis Patients," Nephron, Aug. 1998, 79(4):399-407.
Bonventre, "Dedifferentiation and Proliferation of Surviving Epithelial Cells in Acute Renal Failure," J Am Soc Nephrol, Jun. 2003, 14(Suppl 1):S55-S61.
Bonventre, "Pathophysiology of Acute Kidney Injury: Roles of Potential Inhibitors of Inflammation," Contrib Nephrol, 2007, 156:39-46.
Bonventre et al., "Ischemic acute renal failure: An inflammatory disease?," Kidney Int, Aug. 2004, 66(2):480-485.
Burne et al., "IL-1 and TNF independent pathways mediate ICAM-1/VCAM-1 up-regulation in ischemia reperfusion injury," J Leukoc Biol, Aug. 2001, 70(2):192-198.
Burne-Taney et al., "The role of adhesion molecules and T cells in ischemic renal injury," Curr Opin Nephrol Hypertens, Jan. 2003, 12(1):85-90.
Cai, "Detection and Application for the biomarker of Rental Injury in Early Stage," Laboratory Med Clinic, Jun. 2005, 2:124-127—incl English translation.
Calabrese et al., "Oxidative stress and cellular stress response in diabetic nephropathy," Cell Stress & Chaperones, Jan. 2007, 12(4):299-306—Accession No. XP002705326.
Canani et al., "The Fatty Acid-Binding Protein-2 A54T Polymorphism Is Associated With Renal Disease in Patients With Type 2 Diabetes," Diabetes, Nov. 2005, 54(11):3326-3330.
Caron et al., "Ischemic injury alters endothelial cell properties of kidney cortex: Stimulation of MMP-9," Exp Cell Res., Aug. 2005 (online), 301(1):105-116.
Catania et al., "Role of matrix metalloproteinases in renal pathophysiologies," Am J Physiol Renal Physiol, Dec. 2006 (first published), 292(3):F905-F911.
Chawla et al., "Identifying critically ill patients at high risk for developing acute renal failure: A pilot study," Kidney Int., 2005, 68(5):2274-2280.
Chertow et al., "Acute Kidney Injury, Mortality, Length of Stay, and Costs in Hospitalized Patients," J Am Soc Nephrol, Sep. 2005 (Epub), 16(11):3365-3370.
Choi et al., "Expression of Vascular Endothelial Growth Factor-C and its Receptor mRNA in the Rat Kidney with Ischemia-Reperfusion Injury," Clinical Kidney J, Jun. 2, 2011, 4(Suppl 2):2 pp.
Christenson et al., "Standardization of Cardiac Troponin I Assays: Round Robin of Ten Candidate Reference Materials," Clinical Chemistry, Mar. 2001, 47(3):431-437.
Coca et al., "Biomarkers for the diagnosis and risk stratification of acute kidney injury: A systematic review," Kidney Int, Dec. 2007 (pub online), 73(9):1008-1016.

(56) References Cited

OTHER PUBLICATIONS

Constantin et al., "Plasma neutrophil gelatinase-associated lipocalin is an early marker of acute kidney injury in adult critically ill patients: A prospective study," J Crit Care, 2010, 25(1):176.e1-176.e6.

Cooper, "Effect of tobacco smoking on renal function," Indian J Med Res, Sep. 2006, 124(3):261-268.

Cottone et al., "Endothelin-1 and F2-isoprostane relate to and predict renal dysfunction in hypertensive patients," Nephrol Dial Transpl, Sep. 2008 (advance access pub), 24(2):497-503.

Cruz et al., "North East Italian Prospective Hospital Renal Outcome Survey on Acute Kidney Injury (NEiPHROS-AKI): Targeting the Problem with the RIFLE Criteria," Clin J Amer Soc Nephrol, Mar. 2007 (Epub), 2(3):418-425.

Cutillas et al., "The urinary proteome in Fanconi syndrome implies specificity in the reabsorption of proteins by renal proximal tubule cells," Am J Physiol Renal Physiol, May 2004, 287(3):F353-F364.

Cwirla et al., "Peptides on phage: A vast library of peptides for identifying ligands," Proc Natl Acad Sci USA, Aug. 1990, 87(16):6378-6382.

Daemen et al., "Apoptosis and Chemokine Induction After Renal Ischemia-Reperfusion," Transplantation, Apr. 15, 2001, 71(7):1007-1011.

Daha et al., "Is the proximal tubular cell a proinflammatory cell?," Nephrol Dial Transplant, 2000, 15(Suppl 6):41-43.

De Sá et al., "Leukocyte, Platelet and Endothelial Activation in Patients with Acute Renal Failure Treated by Intermittent Hemodialysis," Am J Nephrol, Jul.-Aug. 2001, 21(4):264-273.

Devarajan, "Cellular and molecular derangements in acute tubular necrosis," Curr Opin Pediatr, Apr. 2005, 17(2):193-199.

Devarajan, "Novel biomarkers for the early prediction of acute kidney injury," Cancer Therapy, Sep. 2005, 3:477-488.

Devarajan, "Update on Mechanisms of Ischemic Acute Kidney Injury," J Am Soc Nephrol, May 2006 (Epub), 17(6):1503-1520.

Devarajan et al., "Proteomics for Biomarker Discovery in Acute Kidney Injury," Semin Nephrol, Nov. 2007, 27(6):637-651.

Devlin et al., "Random Peptide Libraries: A Source of Specific Protein Binding Molecules," Science, Jul. 27, 1990, 249(A967):404-406.

Domanski et al., "Purine and Cytokine Concentrations in the Renal Vein of the Allograft During Reperfusion," Transplant Proc, Jun. 2007, 39(5):1319-1322.

Edelstein, "Biomarkers of Acute Kidney Injury," Adv Chronic Kidney Dis., Jul. 2008, 15(3)222-234.

El Sabbahy et al., "Ischemic kidney injury and mechanisms of tissue repair," Wiley Interdiscip Rev Syst Biol Med, Dec. 2010 (Epub), 3(5):606-618.

Endo et al., "Matrix metalloproteinase-2, matrix metalloproteinase-9, and tissue inhibitor of metalloproteinase-1 in the peripheral blood of patients with various glomerular diseases and their implication in pathogenetic lesions: study based on an enzyme-linked assay and immunohistochemical staining," Clin Exp Nephrol, Dec. 2006, 10(4):253-261.

Etzioni et al., "Combining biomarkers to detect disease with application to prostate cancer," Biostatistics, 2003, 4(4):523-538.

FDA, "European Medicines Agency to Consider Additional Test Results When Assessing New Drug Safety—Collaborative effort by FDA and EMEA expected to yield additional safety data," Jun. 12, 2008, http://www.natap.org/2008/ newsUpdates/071608_01.htm.

FDA News Release, U.S. Food and Drug Administration, FDA allows marketing of the first test to assess risk of developing acute kidney injury, Sep. 5, 2014, https://www.fda.gov/NewsEvents/Newsroom/PressAnnouncements/ucm412910.htm.

Ferguson et al., "Biomarkers of nephrotoxic acute kidney injury," Toxicology, Jan. 2008 (Epub), 245(3):182-193.

Fischer et al., "A readers' guide to the interpretation of diagnostic test properties: clinical example of sepsis," Intensive Care Med, May 2003, 29:1043-1051.

Flynn et al., "Urinary excretion of beta2-glycoprotein-1 (apolipoprotein H) and other markers of tubular malfunction in "non-tubular" renal disease," J Clin Pathol, Jul. 1992, 45(7):561-567.

Frangogiannis, "Chemokines in ischemia and reperfusion," Thromb Haemost, Apr. 2007 (pub online), 97(5):738-747.

Fried et al., "Inflammatory and Prothrombotic Markers and the Progression of Renal Disease in Elderly Individuals," J Am Soc Nephrol, Dec. 2004, 15(12):3184-3191.

Fu et al., "Study on the expression of VEGF, MMP-2 and TIMP-2 in the progression of IgA nephropathy," J Clin Exp Pathol, Oct. 24, 2008, 24(5):573-576.

Fujisaki et al., "Infusion of radiocontrast agents induces exaggerated release of urinary endothelin in patients with impaired renal function," Clin Exp Nephrol, Dec. 2003, 7(4):279-283.

Furuichi et al., "Chemokine/chemokine receptor-mediated inflammation regulates pathologic changes from acute kidney injury to chronic kidney disease," Clin Exp Nephrol, Dec. 2008 (Epub), 13(1):9-14.

Furuichi et al., "Roles of chemokines in renal ischemia/reperfusion injury," Front Biosci, May 1, 2008, 13:4021-4028.

Galkina et al., "Leukocyte Recruitment and Vascular Injury in Diabetic Nephropathy," J Am Soc Nephrol, Jan. 2006 (Epub), 17(2):368-377.

Garcia et al., "Adenosine A2A receptor activation and macrophage-mediated experimental glomerulonephritis," FASEB J, Sep. 2007 (Epub), 22(2):445-454.

Gbadegesin et al., "Plasma and urinary soluble adhesion molecule expression is increased during first documented acute pyelonephritis," Arch Dis Child, Mar. 2002, 86(3):218-221.

Gocze et al., "Urinary Biomarkers TIMP-2 and IGFBP7 Early Predict Acute Kidney Injury after Major Surgery," PLoS ONE, Mar. 23, 2015, DOI:10.1371/journal.pone.0120863, pp. 1-11.

Goes et al., "Effect of Recombinant Human Insulin-Like Growth Factor-1 on the Inflammatory Response to Acute Renal Injury," J Am Soc Nephrol, May 1996, 7(5):710-720.

Goldstein et al., "Renal Angina," Clin J Am Soc Nephrol, 2010, 5(5):943-949.

Grigoryev et al., "The Local and Systemic Inflammatory Transcriptome after Acute Kidney Injury," J Am Soc Nephrol, Jan. 2008 (Epub), 19(3):547-558.

Gümüs et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001, 27(2):133-135.

Gupta et al., "Role of Protein C in Renal Dysfunction after Polymicrobial Sepsis," J Am Soc Nephrol., Mar. 18, 2007, (3):860-867.

Haase et al., "A comparison of the RIFLE and Acute Kidney Injury Network classifications for cardiac surgery-associated acute kidney injury: A prospective cohort study," J Thorac Cardiovasc Surg, Dec. 2009, 138(6):1370-1376.

Han, "Biomarkers for Early Detection of Acute Kidney Injury," Nephrology Rounds, Apr. 2008, 6(4):6 pp.

Han et al., "Upregulation of hyaluronan and its binding receptors in an experimental model of chronic cyclosporine nephropathy," Nephrology (Carlton), Mar. 2010, 15(2):216-224.

Han et al., "Urinary Biomarkers in the Early Diagnosis of Acute Kidney Injury after Cardiac Surgery," Clin J Am Soc Nephrol, Apr. 2009 (Epub), 4(5):873-882.

Han et al., "Urinary biomarkers in the early diagnosis of acute kidney injury," Kidney Int, Dec. 2007 (pub online), 73(7):863-869.

Hanley et al., "The Meaning and Use of the Area under a Receiver Operating Characteristic (ROC) Curve," Radiology, Apr. 1982, 143(1):29-36.

Harpur et al., "Biological Qualification of Biomarkers of Chemical-Induced Renal Toxicity in Two Strains of Male Rat," Toxicol Sci., May 2011 (advance access pub), 122(2):235-252.

Harris et al., "Growth Factors and Cytokines in Acute Renal Failure," Adv Ren Replace Ther, Apr. 1997, 4(2)Suppl 1:43-53.

Hatta et al., "Cytokine Array Comparisons of Plasma from Cycling Fertile Women on Cycle Day 5 and Ovulation," Am J Reprod Immunol, Sep. 2009, 62(3):158-164.

(56) References Cited

OTHER PUBLICATIONS

He et al., "A research on serum, urine and tumor tissue hyaluronate assays for detecting malignant ovarian tumors," Zhonghua Fu Chan Ke Za Zhi, Mar. 1995, 30(3):161-163 (abstract only).
He et al., "Interleukin-18 binding protein transgenic mice are protected against ischemic acute kidney injury," Am J Physiol Renal Physiol, Aug. 2008 (Epub), 295(5):F1414-F1421.
Healy et al., "Apoptosis and necrosis: Mechanisms of cell death induced by cyclosporine A in a renal proximal tubular cell line," Kidney Int, 1998, 54(6):1955-1966.
Herget-Rosenthal et al., "Early detection of acute renal failure by serum cystatin C," Kidney Int, Sep. 2004, 66(3):1115-1122.
Hidaka et al., "Urinary clusterin levels in the rat correlate with the severity of tubular damage and may help to differentiate between glomerular and tubular injuries," Cell Tissue Res, Oct. 2002, 310(3):289-296.
Hirai et al., "Plasma Endothelin-1(ET-1) is a Useful Marker for Renal Dysfunction," Atheroscler Suppl., Jun. 19, 2006, 7(3):60[Mo-P1:65].
Hirschberg et al., "Factors Predicting Poor Outcome In Patients with Acute Renal Failure (ARF)," J Am Soc Nephrol, Sep. 1, 1996, 7(9):1374 [A0644].
Honore et al., "Urinary Tissue Inhibitor of Metalloproteinase-2 and Insulin-Like Growth Factor-Binding Protein 7 for Risk Stratification of Acute Kidney Injury in Patients With Sepsis," Grit Care Med, Oct. 2016, 44(10):1851-1860.
Hoste et al., "RIFLE criteria for acute kidney injury are associated with hospital mortality in critically ill patients: a cohort analysis.," Crit Care, May 2006, 10(3):R73, 10 pp.
Hugo et al., "Thrombospondin 1 precedes and predicts the development of tubulointerstitial fibrosis in glomerular disease in the rat," Kidney Int, Feb. 1998, 53(2):302-311.
Hugo et al., "Thrombospondin in Renal Disease," Nephron Exp Nephrol, 2009, 111(3):e61-e66.
Humphreys et al., "Mesenchymal Stem Cells in Acute Kidney Injury," Annu Rev Med., 2008, 59:311-325.
Iglesias et al., "Thyroid Dysfunction and Kidney Disease (Revised version)," Eur J Endocrinol, Dec. 18, 2008, pp. 1-32 retrieved from URL://www.eje.org/content!early/2008/12/18/EJE-08-0837.full.pdf.
Jaimes et al., "The systemic inflammatory response syndrome (SIRS) to identify infected patients in the emergency room," Intensive Care Med, Jun. 2003, 29:1368-1371.
Jang et al., "The innate immune response in ischemic acute kidney injury," Clin Immunol, Oct. 2008 (Epub), 130(1):41-50.
Jonsson, "The role of fibroblast growth factor 23 in renal disease," Nephrol Dial Transplant, Mar. 2005, 20(3):479-482.
Julian et al., "Sources of Urinary Proteins and their Analysis by Urinary Proteomics for the Detection of Biomarkers of Disease," Proteomics Clin Appl., Aug. 26, 2009, 3(9):1029-1043.
Jung et al., "Diagnostic Significance of Urinary Enzymes in Detecting Acute Rejection Crises in Renal Transplant Recipients Depending on Expression of Results Illustrated Through the Example of Alanine Aminopeptidase," Clin Biochem, Aug. 1985, 18(4):257-260.
Kadiroglu et al., "The Evaluation of Effects of Demographic Features, Biochemical Parameters, and Cytokines on Clinical Outcomes in Patients with Acute Renal Failure," Renal Failure, 2007, 29(4):503-508.
Kalousová et al., "Soluble Receptor for Advanced Glycation End Products in Patients With Decreased Renal Function," Am J Kidney Dis, Mar. 2006, 47(3):406-411.
Kamata et al., "Up-regulation of glomerular extracellular matrix and transforming growth factor-beta expression in RF/J mice," Kidney Int, Mar. 1999, 55(3):864-876.
Kamimoto et al., "Hepatocyte growth factor prevents multiple organ injuries in endotoxemic mice through a heme oxygenase-1-dependent mechanism," Biochem Biophys Res Commun, Jan. 2009 (Epub), 380(2):333-337.
Kasahara et al., "Clinical Significance of Serum Oxidized Low-Density Lipoprotein/beta2-Giycoprotein I Complexes in Patients with Chronic Renal Diseases," Nephron Clin Pract, 2004, 98(1):c15-c24.
Kashani et al., "Discovery and validation of cell cycle arrest biomarkers in human acute kidney injury," Critical Care, Feb. 2013, 17(R25):1-12.
KDIGO Clinical Practice Guideline for Acute Kidney Injury, Official Journal of the International Society of Nephrologoy, Kidney International Supplements, Mar. 2012, 2(suppl 1):1-141.
Kehoe et al., "Elevated Plasma Renin Activity Associated with Renal Dysfunction," Nephron, 1986, 44(1):51-57 (abstract only).
Keightley, "A comparison of manual and robotic pipetting for plate-based assays," Laboratory Practice, Journal, 1989, 38(10):53-55—Abstract only.
Kellum, "Acute kidney injury," Crit Care Med, 2008, 36(4) Suppl:S141-S145.
Kellum et al., "Definition and Classification of Acute Kidney Injury," Nephron Clin Pract, Sep. 2008, 109(4):c182-c187.
Keyes et al., "Early diagnosis of acute kidney injury in critically ill patients," Expert Rev Mol Diagn, Jul. 2008, 8(4):455-464.
Khanna et al., "Expression of TGF-beta and fibrogenic genes in transplant recipients with tacrolimus and cyclosporine nephrotoxicity," Kidney Int, Dec. 2002, 62(6):2257-2263.
Kharasch et al., "Gene Expression Profiling of Nephrotoxicity from the Sevoflurane Degradation Product Fluoromethyl-2,2-difluoro-1-(trifluoromethyl)vinyl Ether ("Compound A") in Rats," Toxicol Sci, Oct. 2005 (advance access pub), 90(2):419-431.
Kierdorf et al., "Continuous Renal Replacement Therapies Versus Intermittent Hemodialysis in Acute Renal Failure: What Do We Know?," American Journal of Kidney Diseases, Nov. 1996, 28(5)(Suppl 3):S90-S96.
Kiley et al., "Urinary biomarkers: the future looks promising," Kidney Int, Jul. 2009, 76(2):133-134.
Kilis-Psirusinska et al., [Levels of selected soluble adhesion molecules in blood serum of children with chronic glomerulonephritis]. Pol Merkur Lekarski. Apr. 2001;10(58):247-249—incl English translation abstract only.
Kilis-Pstrusinska et al., "Serum levels of soluble adhesion molecules in children with glomerulonephritis (GN)," Nephrol Dialysis Transplant, Jun. 2001, 16:A62.
Kimmel et al., "Immunologic function and survival in hemodialysis patients," Kidney Int, Jul. 1998, 54(1):236-244.
Kingsmore et al., "Multiplexed protein profiling on antibody-based microarrays by rolling circle amplification," Current Opin Biotechnol, Feb. 2003, 14(1):74-81.
Kinsey et al., "Inflammation in Acute Kidney Injury," Nephron Exp Nephrol, Sep. 2008 (Epub), 109(4):e102-e107.
Koo et al., "Cadaver versus living donor kidneys: Impact of donor factors on antigen induction before transplantation," Kidney Int, Oct. 1999, 56(4):1551-1559.
Kos et al., "Cathepsins B, H, and L and Their Inhibitors Stefin A and Cystatin C in Sera of Melanoma Patients," Clin Cancer Res, Oct. 1997, 3(10):1815-1822.
Kunugi et al., "Inhibition of matrix metalloproteinases reduces ischemia-repertusion acute kidney injury," Lab Invest, Oct. 2010 (Epub), 91(2):170-180.
Kutsukake et al., "Circulating IGF-binding protein 7 (IGFBP7) levels are elevated in patients with endometriosis or undergoing diabetic hemodialysis," Reproductive Biology and Endocrinology, 2008, 6(54):1-6.
Lan, "Clinical significance of determination of serum hyaluronic acid, type III procollagen, collagen IV and laminin in patients with nephropathy," J Guangxi Med Univ., Oct. 2002, 19(5):655-656—incl Engl transl of abstract only.
Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004, 43(2):244-253.
Lang et al., "Heat Shock Protein 60 Is Released in Immune-Mediated Glomerulonephritis and Aggravates Disease: In Vivo Evidence for an Immunologic Danger Signal," J Am Soc Nephrol, Dec. 2004 (Epub), 16(2):383-391.

(56) References Cited

OTHER PUBLICATIONS

Lapsley et al., "Beta2-glycoprotein-1 (apolipoprotein H) excretion in chronic renal tubular disorders: Comparison with other protein markers of tubular malfunction," J Clin Pathol, Oct. 1991, 44(10):812-816.

Larsson et al., "Circulating concentration of FGF-23 increases as renal function declines in patients with chronic kidney disease, but does not change in response to variation in phosphate intake in healthy volunteers," Kidney Int, Dec. 2003, 64(6):2272-2279.

Lassnigg et al., "Minimal Changes of Serum Creatinine Predict Prognosis in Patients after Cardiothoracic Surgery: A Prospective Cohort Study," J Am Soc Nephrol, 2004, 15(6):1597-1605.

Lemay et al., "Prominent and Sustained Up-Regulation Of GP130-Signaling Cytokines and of the Chemokine MIP-2 in Murine Renal Ischemia-Reperfusion Injury," Transplantation, Mar. 15, 2000, 69(5):959-63.

Li et al., Predictive value of RIFLE classification on prognosis of critically ill patients with acute kidney injury treated with continuous renal replacement therapy, Chin Med J (Engl), May 5, 2009, 122(9):1020-1025.

Liu et al., "Predictive and pathogenetic value of plasma biomarkers for acute kidney injury in patients with acute lung injury," Crit Care Med, Dec. 2007, 35(12):2755-2761.

Liu et al., "Serum Interleukin-6 and interleukin-8 are early biomarkers of acute kidney injury and predict prolonged mechanical ventilation in children undergoing cardiac surgery: a case-control study," Critical Care, Jul. 2009 (Epub), 13(4):R104 (9 pp).

Llewelyn et al., "Diagnosis of infection in sepsis," Intensive Care Med, 2001, 27 Suppl 1:S10-S32.

Lopes-Virella et al., "Urinary High Density Lipoprotein in Minimal Change Glomerular Disease and Chronic Glomerulopathies," Clin Chim Acta, 1979, 94(1):73-81.

López-Bermejo et al., "Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues," J Clin Endocrinol Metab, Jul. 2003, 88(7):3401-3408.

Lu et al., "Increased Macrophage Infiltration and Fractalkine Expression in Cisplatin-Induced Acute Renal Failure in Mice," J Pharmacol Exp Ther, Oct. 2007 (Epub), 324(1):111-117.

Lu et al., "Biomarker detection in the integration of multiple multi-class genomic studies," Bioinformatics, 2010, 26(3):333-340.

Maccallum et al., "Antibody-antigen Interactions: Contact Analysis and Binding Site Topography," J Mol Biol, 1996, 262:732-745.

Maddens et al., "Chitinase-like Proteins are Candidate Biomarkers for Sepsis-induced Acute Kidney Injury," Mol Cell Proteomics, Jan. 10, 2012, 11(6):1-13.

Maier et al., "Massive Chemokine Transcription in Acute Renal Failure Due to Polymicrobial Sepsis," Shock, Aug. 2000, 14(2):187-192.

Malm et al., "Changes in the plasma levels of vitamin K-dependent proteins C and S and of C4b-binding protein during pregnancy and oral contraception," Br J Haematol, Apr. 1988, 68(4):437-443.

Malyszko et al., "Visfatin and apelin, new adipocytokines, and their relation to endothelial function in patients with chronic renal failure," Adv Med Sci, 2008, 53(1):32-36.

Mamtani et al., "A simple method to combine multiple molecular biomarkers for dichotomous diagnostic classification," BMC Bioinformatics, Oct. 10, 2006, 7:442, 12 pp.

Mast et al., "Clinical utility of the soluble transferrin receptor and comparison with serum ferritin in several populations," Clin Chem, Jan. 1998, 44(1):45-51.

Matousovic et al., "IgA-containing immune complexes in the urine of IgA nephropathy patients," Nephrol Dial Transplant, Jun. 2006 (Epub), 21(9):2478-2484.

Matsuda et al., "Beta2-Glycoprotein I—Dependent and-Independent Anticardiolipin Antibody in Patients with End-Stage Renal Disease," Thromb Res., Oct. 15, 1993, 72(2):109-117.

Matsuzaka et al., "Relationship between vitamin K dependent coagulation factors and anticoagulants (protein C and protein S) in neonatal vitamin K deficiency," Arch Dis Childhood, Mar. 1993, 68:297-302.

Mattes, "Experience With a Biomarker Consortium," CPath Predictive Safety Training Consortium, Critical Path Institute, 48 pp.

Mazanowska et al., "Imbalance of metallaproteinase/tissue inhibitors of metalloproteinase system in renal transplant recipients with chronic allograft injury," Transplant Proc, Oct. 2011, 43(8):3000-3003.

Mccullough et al., "Contrast-Induced Nephropathy (CIN) Consensus Working Panel: Executive Summary," Rev Cardiovasc Med, 2006, 7(4):177-197.

Meersch et al., "Urinary TIMP-2 and IGFBP7 as Early Biomarkers of Acute Kidney Injury and Renal Recovery following Cardiac Surgery," PLoS One, Mar. 2014; 9(3):e93460, 9 pp.

Meersch et al., "Validation of Cell-Cycle Arrest Biomarkers for Acute Kidney Injury after Pediatric Cardiac Surgery," PLoS One, Oct. 2014, 9(10):e110865. doi: 10.1371/journal.pone.0110865.

Mehran et al., "A Simple Risk Score for Prediction of Contrast-Induced Nephropathy After Percutaneous Coronary Intervention: Development and Initial Validation," J Am Coll Cardiol, Oct. 2004, 44(7):1393-1399.

Mehta et al., "Acute Kidney Injury Network: report of an initiative to improve outcomes in acute kidney injury," Crit Care, 2007, 11(2):R31 (8 pages).

Melnikov et al., "Impaired IL-18 processing protects caspase-1-deficient mice from ischemic acute renal failure," J Clin Invest, May 2001, 107(9):1145-1152.

Mezzano et al., "Endothelial Cell Markers in Chronic Uremia: Relationship with Hemostatic Defects and Severity of Renal Failure," Thromb Res, Dec. 15, 1997, 88(6):465-472.

Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991, 6(4):232-237.

Mishra et al., "Neutrophil gelatinase-associated lipocalin (NGAL) as a biomarker for acute renal injury after cardiac surgery," Lancet, Apr. 2005, 365(9466):1231-1238.

Miura et al., "Neutralization of Gro(alpha) and Macrophage Inflammatory Protein-2 Attenuates Renal Ischemia/Reperfusion Injury," Am J Pathol., Dec. 2001, 159(6):2137-2145.

Molls et al., "Keratinocyte-derived chemokine is an early biomarker of ischemic acute kidney injury," Am J Physiol Renal Physiol, Dec. 2005 (Epub), 290(5):F1187-F1193.

Montagna et al., "Impairment of cellular redox status and membrane protein activities in kidneys from rats with ischemic acute renal failure," Biochim Biophys Acta, 1998, 1407(2):99-108.

Musial et al., "Soluble Adhesion Molecules in Chronic Renal Failure (CRF) Children Treated Conservatively," Nephrol Dialysis Transplant, 2002, 17(Abstracts Suppl 1):232.

Musial et al., "The Heat Shock Protein Profile in Children with Chronic Kidney Disease," Pent Dial Int., Jan. 2010 (Epub), 30(2):227-232.

Nambi et al., "Down regulation of kidney neutral endopeptidase mRNA, protein and activity during acute renal failure: Possible mechanism for ischemia-induced acute renal failure in rats?," Mol Cell Biochem, Jul. 1999, 197(1-2):53-59.

Nejat et al., "Urinary cystatin C is diagnostic of acute kidney injury and sepsis, and predicts mortality in the intensive care unit," Critical Care, 2010, 14(3):R85, 13 pp.

Nelson et al., "A computer program for calculating antibody affinity constants," Comput Methods Programs Biomed, Jul.-Aug. 1988, 27(1):65-68.

Neziri et al., "Cloning and molecular characterization of Dashurin encoded by C20orf116, a PCI-domain containing protein," Biochim Biophys Acta, Dec. 2009 (Epub), 1800(4):430-438.

Nguyen et al., "Biomarkers for the early detection of acute kidney injury," Pediatr Nephrol, Mar. 2007 (Epub), 23:2151 https://doi.org/10.1007/s00467-007-0470-x.

(56) References Cited

OTHER PUBLICATIONS

Nguyen et al., "Heparin-Binding EGF-Like Growth Factor Is Up-Regulated in the Obstructed Kidney in a Cell-and Region-Specific Manner and Acts to Inhibit Apoptosis," Am J Pathol, Mar. 2000, 156(3):889-898.
Nishiyama et al., "Up-Regulation of Galectin-3 in Acute Renal Failure of the Rat," Am J Pathol, Sep. 2000, 157(3):815-823.
Norman et al., "Progressive Renal Disease: Fibroblasts, Extracellular Matrix, and Integrins," Exp Nephrol, Mar.-Apr. 1999, 7(2):167-177.
Obuchowski et al., "ROC Curves in Clinical Chemistry: Uses, Misuses, and Possible Solutions," Clinical Chemistry, May 2004 (Epub), 50(7):1118-1125.
Oh, "The insulin-like growth factor system in chronic kidney disease: Pathophysiology and therapeutic opportunities," Kidney Res Clin Pract, Jan. 2012 (Epub);31:26-37.
Ohno et al., "Prognostic significance of tenascin-C expression in clear cell renal cell carcinoma," Oncol Rep, Sep. 2008, 20(3):511-516.
Ozer et al., "A panel of urinary biomarkers to monitor reversibility of renal injury and a serum marker with improved potential to assess renal function," Nat Biotechnol, May 2010, 28(5):486-494.
Pajenda et al., "NephroCheck data compared to serum creatinine in various clinical settings," BMC Nephrology, Dec. 9, 2015, 16(206):2-7.
Parikh et al., "New biomarkers of acute kidney injury," Crit Care Med, Apr. 2008, 36(4 Suppl):S159-S165.
Parikh et al., "Urinary IL-18 is an early predictive biomarker of acute kidney injury after cardiac surgery," Kidney Int, May 2006 (Epub), 70(1):199-203.
Paul, "Fundamental Immunology," Third Edition, Structure and Function of Immunoglobulins, 1993, 8:292-295.
Perco et al., "Protein biomarkers associated with acute renal failure and chronic kidney disease," Eur J Clin Invest, Nov. 2006, 36(11):753-763.
Picard et al., "Origin of renal myofibroblasts in the model of unilateral ureter obstruction in the rat," Histochem Cell Biol, May 2008 (Epub), 130(1):141-155.
Praught et al., "Are small changes in serum creatinine an important risk factor?," Curr Opin Nephrol Hypertens, 2005, 14(3):265-270.
Price, "Abrupt Changes In Prostate-Specific Antigen Concentration in Acute Renal Failure," Clin Chem, Jan. 1993, 39(1):161-162.
Prozialeck et al., "Cell Adhesion Molecules in Chemically-Induced Renal Injury," Pharmacol Ther, Jan. 2007 (Epub), 114(1):74-93.
Radford, Jr. et al., "Predicting Renal Outcome in IgA Nephropathy," J Am Soc Nephrol, Feb. 1997, 8(2):199-207.
Rajashekar et al., "Systemic diseases with renal manifestations," Prim Care, Jun. 2008, 35(2):297-328.abstract retrieved from URL:www.ncbi.nlm.nih.gov/pubmed/18486717.
Ramesh et al., "Endotoxin and cisplatin synergistically induce renal dysfunction and cytokine production in mice," Am J Physiol Renal Physiol, May 2007 (Epub), 293(1):F325-F332.
Ramesh et al., "TNF-α mediates chemokine and cytokine expression and renal injury in cisplatin nephrotoxicity," J Clin Invest, Sep. 2002, 110(6):835-842.
Ramirez et al., "Prospective Study on Autoantibodies Against Apolipoprotein H (Beta2GPI) in Several Clinical Parameters From Patients With Terminal Renal Failure and Functioning Renal Transplants," Transplantation Proceedings, Jul.-Aug. 2009, 41(6):2370-2372.
Ricci et al., "The RIFLE criteria and mortality in acute kidney injury: A systematic review," Kidney Int, Dec. 2007 (Epub), 73(5):538-546.
Ridker, "C-Reactive Protein: A Simple Test to Help Predict Risk of Heart Attack and Stroke," Circulation, Sep. 2003, 108:e81-e85.
Rini et al., "Renal cell carcinoma," Lancet, Mar. 2009, 373:1119-1132.
Ronco et al., "The concept of risk and the value of novel markers of acute kidney injury," Critical Care, Feb. 2013, 17(117):1-2.

Ronco et al., "Potential Interventions in Sepsis-Related Acute Kidney Injury," Clin J Am Soc Nephrol, Jan. 2008 (Epub), 3:531-544.
Rosenkranz et al., "P-selectin deficiency exacerbates experimental glomerulonephritis: a protective role for endothelial P-selectin in inflammation," J Clin Invest, Mar. 1999, 103(5):649-659.
Rouschop et al., "Pre-transplant plasma and cellular levels of CD44 correlate with acute renal allograft rejection," Nephrol Dial Transplant, Oct. 2005, 20(10):2248-2254.
Rouschop et al., "Renal expression of CD44 correlates with acute renal allograft rejection," Kidney Int, Jul. 2006 (Epub), 70(6):1127-1134.
Sato et al., "Midkine Is Involved in Neutrophil Infiltration into the Tubulointerstitium in Ischemic Renal Injury," J Immunol, Sep. 15, 2001, 167(6):3463-3469.
Schaefer et al., "Urinary excretion of cathepsin B and cystatins as parameters of tubular damage," Kidney Int Suppl, Nov. 1994, 47:S64-S67.
Schaefer et al., "Insulin-like Growth Factor-I and the Kidney. Insulin-like Growth Factors," Kluwer Academic/Plenum Publishers, New York, 2003:244-261.
Schena et al., "EGF and MCP-1 Urinary Excretion Is a Suitable Prognostic Marker in IgA Nephropathy," J Am Soc Of Nephrology, Meeting of The American Society of Nephrology, Sep. 1, 2002, 13(Program and Abstracts Issue): 458A.
Schiffer et al., "Activated Renal Macrophages Are Markers of Disease Onset and Disease Remission in Lupus Nephritis," J Immunol, Feb. 2008, 180(3):1938-1947.
Schmaldienst et al., "Angiogenin: A Novel Inhibitor of Neutrophil Lactoferrin Release during Extracorporeal Circulation," Kidney Blood Press Res, 2003, 26(2):107-112.
Schmidt et al., "Sexual hormone abnormalities in male patients with renal failure," Nephrol Dial Transplant, Mar. 2002, 17(3):368-371.
Schulz et al., "Endothelin-1 as an Early Prognostic Marker in Acute Renal Failure (ARF) and Sepsis," Kidney Blood Press Res, 2000, 23(3-5):341-342.
Scott et al., "Searching for Peptide Ligands with an Epitope Library," Science, Jul. 27, 1990, 249:386-390.
Segawa et al., "In situ expression and soluble form of P-selectin in human glomerulonephritis," Kidney Int, Oct. 1997, 52(4):1054-1063.
Segerer et al., "Chemokines, Chemokine Receptors, and Renal Disease: From Basic Science To Pathophysiologic and Therapeutic Studies," J Am Soc Nephrol, Jan. 2000, 11(1):152-176.
Senatorski et al., "Urine activity of cathepsin B, collagenase and urine excretion of TGF-beta1 and fibronectin in membranous glomerulonephritis," Res Exp Med (Berl), Dec. 1998, 198(4):199-206.
Severini et al., "Diagnostic significance of urinary enzymes: development of a high performance liquid chromatographic method for the measurement of urinary lysozyme," Clinica Chimica Acta, Feb. 1987, 163(1):97-103.
Sharma et al., "Two-dimensional fluorescence difference gel electrophoresis analysis of the urine proteome in human diabetic nephropathy," Proteomics, Jul. 2005, 5(10):2648-2655.
Shek et al., "Robotic enzyme-linked immunosorbent assay (ELISA) system for rodent serology: modifications to enhance capacity, throughput and sensitivity," Proc Int Symp Lab Autom Rob, Conference 1992, pp. 282-298—Abstract only.
Shimoda et al., "Cathepsin G Is Required for Sustained Inflammation and Tissue Injury after Reperfusion of Ischemic Kidneys," Am J Pathol, Mar. 2007, 170(3):930-940.
Shlipak et al., "Elevations of Inflammatory and Procoagulant Biomarkers in Elderly Persons With Renal Insufficiency," Circulation, Jan. 2003, 107(1):87-92.
Shoji et al., "Plasma angiopoietin-like protein 3 (ANGPTL3) concentration is associated with uremic dyslipidemia," Atherosclerosis, May 2009 (Epub), 207(2):579-584.
Siew et al., "Biological Markers of Acute Kidney Injury," J Am Soc Nephrol, 2011, 22:810-820.
Simmons et al., "Plasma cytokine levels predict mortality in patients with acute renal failure," Kidney Int, Apr. 2004, 65(4):1357-1365.

(56) References Cited

OTHER PUBLICATIONS

Song et al., "Expression of TRAIL, DR4, and DR5 in Kidney and Serum From Patients Receiving Renal Transplantation," Transplant Proc, Jun. 2004, 36(5):1340-1343.
Stafford-Smith et al., "Acute Kidney Injury and Chronic Kidney Disease After Cardiac Surgery," Adv Chronic Kidney Dis, Jul. 2008, 15(3):257-277.
Stampfer et al., "Risk Factor Criteria," Circulation, 2004, 109(25 Suppl 1):IV-3-IV-5.
Staško et al., "Soluble P-Selectin During a Single Hemodialysis Session in Patients With Chronic Renal Failure and Erythropoietin Treatment," Clin Appl Thromb Hemost, Oct. 2007, 13(4):410-415.
Stenvinkel et al., "High Serum Hyaluronan Indicates Poor Survival in Renal Replacement Therapy," Am J Kidney Dis, Dec. 1999, 34(6):1083-1088.
Stuard et al., "Soluble Adhesion Molecules in Chronic Renal Failure Patients," Nephrol Dialysis Transplant, 1997, 12(9):A100.
Su et al., "Diagnostic value of urine sTREM-1 for sepsis and relevant acute kidney injuries: a prospective study," Crit Care, 2011, 15:R250, pp. 1-10.
Sun et al., "A Survey on the Relationship between the Epidermal Growth Factor and Renal Function," Int J Transpl Hemopurific, Dec. 31, 2006, 4(1):41-44—incl English translation abstract only.
Sun et al., "Enhanced Expression of ANGPTL2 in the Microvascular Lesions of Diabetic Glomerulopathy," Nephron Exp Nephrol, Mar. 2007, 105(4):e117-e123.
Supavekin et al., "Differential gene expression following early renal ischemia/repertusion," Kidney Int, May 2003, 63(5):1714-1724.
Sutton, "Alteration of microvascular permeability in acute kidney injury," Microvasc Res, Sep. 2008 (Epub), 77(1):4-7.
Sutton et al., "Injury of the renal microvascular endothelium alters barrier function after ischemia," Am J Physiol Renal Physiol, Apr. 2003 (Epub), 285(2):F191-F198.
Sutton et al., "Microvascular endothelial injury and dysfunction during ischemic acute renal failure," Kidney Int, Nov. 2002, 62(5):1539-1549.
Sykes et al., "Analytical Relationships Among Biosite, Bayer, and Roche Methods for BNP and NT-proBNP," Am J Clin Pathol, Apr. 2005, 123(4):584-590.
Symon et al., "The endogenous insulin-like growth factor system in radiocontrast nephropathy," Am J Physiol, Mar. 1998, 274(3 Pt 2):F490-F497.
Takada et al., "The Cytokine-adhesion Molecule Cascade in Ischemia/Reperfusion Injury of the Rat Kidney," Inhibition by a Soluble P-selectin Ligand, J Clin Invest, Jun. 1997, 99(11):2682-2690.
Tan et al., "The level of urinary secretory immunoglobulin A (sIgA) of patients with IgA nephropathy is elevated and associated with pathological phenotypes," Clin Exp Immunol, Jan. 2009 (Epub), 156(1):111-116.
Tao et al., "Expression of 60-kDa and Inducible 70-kDa Stress Proteins in Gentamicin-Induced Acute Renal Failure," Clin Exp Nephrol, Jul. 1997, 1:254-260.
Tary-Lehmann et al., "Enzyme-Linked Immunosorbent Assay Spot Detection of Interferon-Gamma and Interleukin 5—Producing Cells as a Predictive Marker for Renal Allograft Failure," Transplantation, Jul. 27, 1998, 66(2):219-224.
Taulan et al., "Comprehensive analysis of the renal transcriptional response to acute uranyl nitrate exposure," BMC Genomics, Jan. 11, 2006, 7(2):1-14.
Teppo et al., "Soluble Intercellular Adhesion Molecule-1 (sICAM-1) after Kidney Transplantation: The Origin and Role of Urinary sICAM-1?," Transplantation, Apr. 27, 2001, 71(8):1113-1119.
Thakar et al., "A Clinical Score to Predict Acute Renal Failure after Cardiac Surgery," J Am Soc Nephrol, Nov. 2004 (Epub), 16:162-168.
Thakar et al., "Identification of thrombospondin 1 (TSP-1) as a novel mediator of cell injury in kidney ischemia," J Clin Invest, Nov. 2005 (Epub), 115(12):3451-3458.
Thiele et al., "AKI Associated with Cardiac Surgery," Clin J Ann Soc Nephrol, Nov. 2014 (Epub), 10:500-514.

Thorburn et al., "CXC and CC chemokines induced in human renal epithelial cells by inflammatory cytokines," APMIS, Jul. 2009, 117(7):477-487.
Thurman et al., "C3a Is Required for the Production of CXC Chemokines by Tubular Epithelial Cells after Renal Ishemia/Repertusion," J Immunol, Feb. 1, 2007, 178:1819-1828.
Timoshanko et al., "Interleukin-12 from Intrinsic Cells Is an Effector of Renal Injury in Crescentic Glomerulonephritis," J Am Soc Nephrol, Mar. 2001, 12(3):464-471.
Torres et al., "The ratio of epidermal growth factor to monocyte chemotactic peptide-1 in the urine predicts renal prognosis in IgA nephropathy," Kidney Int, Oct. 2007 (Epub), 73(3):327-333.
Triage BNP Test Product Insert: Rapid Quantitative Test B-type Natriuretic Peptide, Alere Catalog #98000XR, 2011, 28 pages.
Vaidya et al., "Biomarkers of Acute Kidney Injury," Annu Rev Pharmacol Toxicol, Oct. 2007 (pub online), 48:463-493.
Vaidya et al., "Mechanistic biomarkers for cytotoxic acute kidney injury," Expert Opin Drug Metab Toxicol, Oct. 2006, 2(5):697-713.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Van Erp et al., "Application of a Sol Particle Immunoassay to the Determination of Affinity Constants of Monoclonal Antibodies," J Immunoassay, 1991, 12(3):425-443.
Vanhoutte et al., "Biomarker discovery with SELDI-TOF MS in human urine associated with early renal injury: evaluation with computational analytical tools," Nephrol Dial Transplant, Jul. 2007 (Epub), 22(10):2932-2943.
Villanueva et al., "Ischemic acute renal failure induces the expression of a wide range of nephrogenic proteins," Am J Physiol Regul Integr Comp Physiol, Nov. 2005 (Epub), 290(4):R861-R870.
Vonderscher, "Biomarker of Drug Induced Kidney Injury Qualification for Regulatory Decision Making," (CRADA). IOM/FDA, Silver Spring, MD, Apr. 2007, 23:1-31.
Voshol et al., "Evaluation of Biomarker Discovery Approaches to Detect Protein Biomarkers of Acute Renal Allograft Rejection," J Proteome Res. Jul.-Aug. 2005;4(4):1192-1199 (abstract only).
Waikar et al.."Diagnosis, Epidemiology and Outcomes of Acute Kidney Injury," Clin J Am Soc Nephrol, Mar. 2008 (Epub), 3:844-861.
Waikar et al., "Imperfect Gold Standards for Kidney Injury Biomarker Evaluation," J Am Soc Nephrol, Oct. 2011 (Epub), 23(1):13-21.
Wan et al., "The pathogenesis of septic acute renal failure," Curr Opin Crit Care, Dec. 2003;9(6):496-502.
Wang et al., "Netrin-1 and kidney injury. I. Netrin-1 protects against ischemia-reperfusion injury of the kidney," Am J Physiol Renal Physiol, Jan. 2008 (Epub), 294(4):F739-F747.
Wang et al., "Validation of putative genomic biomarkers of nephrotoxicity in rats," Toxicology, Jan. 2008 (Epub), 246:91-100.
Ward et al., "Binding activities of a repertoire of single immunoglobulin variable domains secreted from *Escherichia coli*," Nature, Oct. 12, 1989, 341:544-546.
Wen et al., "One dose of cyclosporine A is protective at initiation of folic acid-induced acute kidney injury in mice," Nephrol Dial Transplant, Jan. 2012 (Epub), 27:3100-3109.
Wetz et al., "Quantification of urinary TIMP-2 and IGFBP-7: an adequate diagnostic test to predict acute kidney injury after cardiac surgery?," Critical Care, Jan. 2015, 19:3, pp. 1-7.
Wijeysundera et al., "Derivation and Validation of a Simplified Predictive Index for Renal Replacement Therapy After Cardiac Surgery," JAMA, Apr. 25, 2007, 297:1801-1809.
Wilson et al., "Simplified conjugation chemistry for coupling peptides to F(ab') fragments: autologous red cell agglutination assay for HIV-1 antibodies," J Immunol Methods, 1994, 175:267-273.
Wilson et al., "Urinary Lysozyme: III. Lysozymuria in Children with the Nephrotic Syndrome," J Pediatr, Feb. 1950, 36(2):199-211.
Winchester et al., "Sorbents in Acute Renal Failure and End-Stage Renal Disease: Middle Molecule and Cytokine Removal," Blood Purif, 2004, 22(1):73-77.
Witzgall et al., "Localization of Proliferating Cell Nuclear Antigen, Vimentin, c-Fos, and Clusterin in the Postischemic Kidney: Evidence for a Heterogenous Genetic Response among Nephron Seg-

(56) References Cited

OTHER PUBLICATIONS ments, and a Large Pool of Mitotically Active and Dedifferentiated Cells," J Clin Invest, May 1994, 93:2175-2188.

Yan et al., "Expression of MMP-2 and TIMP-1 in renal tissue of patients with chronic active antibody-mediated renal graft rejection," Diagn Pathol, Oct. 12, 2012;7:141.

Yang et al., "Acute renal failure during sepsis: Potential role of cell cycle regulation," J Infect, Apr. 2009 (Epub), 58:459-464.

Yang et al., Frequency of anti-bactericidal/permeability-increasing protein (BPI) and anti-azurocidin in patients with renal disease, Clin Exp Immunol, Jul. 1996, 105(1):125-131.

Yang et al., "Remote Ischemic Preconditioning for Prevention of Acute Kidney Injury: A Meta-analysis of Randomized Controlled Trials," Am J Kidney Dis,Jun. 2014 (Epub), 64(4):574-583.

Yarmush et al., "Coupling of antibody-binding fragments to solid-phase supports: site-directed binding of F(ab')2 fragments," J Biochem Biophys Methods, 1992, 25:285-297.

Yasuda et al., "Insulin like growth factor-1 increases p21 expression and attenuates cisplatin-induced acute renal injury in rats," Clin Exp Nephrol, Mar. 2004, 8:27-35.

Yasuda et al., "Simvastatin improves sepsis-induced mortality and acute kidney injury via renal vascular effects," Kidney Int, May 2006, 69(9):1535-1542.

Yu et al., "Urinary biomarkers trefoil factor 3 and albumin enable early detection of kidney tubular injury," Nat Biotechnol, May 2010, 128(5):470-477.

Yuan et al., "Combining Multiple Biomarker Models in Logistic Regression," Biometrics, Jun. 2008, 64:431-439.

Yuen et al., "Ischemic and Nephrotoxic Acute Renal Failure are Distinguished by their Broad Transcriptomic Responses," Physiol Genomics, Feb. 2006 (Epub), 25(3):375-386.

Zaffanello et al., "Early diagnosis of acute kidney injury with urinary biomarkers in the newborn," J Matern-Fetal Neonatal Med, Oct. 2009, 22(Suppl 3):62-66.

Zager et al., "Proximal tubular cytochrome c efflux: Determinant, and potential marker, of mitochondrial injury," Kidney Int, Jun. 2004, 65(6):2123-2134.

Zarjou et al., "Sepsis and Acute Kidney Injury," J Am Soc Nephrol, 2011, 22:999-1006.

Zhang et al., "The level of serum secretory IgA of patients with IgA nephropathy is elevated and associated with pathological phenotypes," Nephrol Dial Transplant, Oct. 2007 (Epub), 23(1):207-212.

Zheng et al., "Antiphospholipid antibody profiles in lupus nephritis with glomerular microthrombosis: a prospective study of 124 cases," Arthritis Research & Therapy, Jun. 2009, 11(3):R93;1-9.

Zhu et al., "Expression of Urinary Epidermal Growth Factor and Renal Function," J Clin Urol, Dec. 31, 1998, 13(8):374-379—incl English transl abstract only.

Official Action dated Nov. 28, 2019, in Chinese application (201780045564.9).

International Search Report and Written Opinion dated Sep. 1, 2017, in PCT/US2017/036227.

Chindarkar et al., "Reference intervals of urinary acute kidney injury (AKI) markers [IGFBP7]·[TIMP2] in apparently healthy subjects and chronic comorbid subjects without AKI," Clinica Chimica Acta, 2016, 452:32-37.

Wasaung et al., "Biomarkers of renal function, which and when?," Clinica Chimica Acta, 2015, 438:350-357.

Wiki: "Chronic kidney disease", Jan. 3, 2020, Retrieved from the internet: URL:https://en.wikipedia.org/wiki/Chronic_kidney_disease [retrieved on Jan. 21, 2020].

Official Action dated Jul. 9, 2020, issued in Chinese application (201780045564.9).

Extended European Search Report dated Jul. 24, 2020, in European application 17810896.5.

Partial Supplementary Search Report dated Jan. 21, 2020, in European application 17810896.5.

Hoste et al., "Derivation and validation of cutoffs for clinical use of cell cycle arrest biomarkers," Nephrol Dial Transplant, 2014, 29:2054-2061.

Inker et al., "KDOQI US Commentary on the 2012 KDIGO Clinical Practice Guideline for he Evaluation and Management of CKD," Am J Kidney Dis, 2014, 63(5):713-735.

Klein et al., "Renal replacement therapy in acute kidney injury," M edizinische Klinik, Urban & Vogel, Munich, May 2, 2017, 112(5):437-443 (in German, includes English abstract on p. 439; cited by EPO in document D10).

Ostermann et al., "Patient Selection and Timing of Continuous Renal Replacement Therapy," Blood Purif, 2016, 42:224-237.

Pilarczyk et al., "Tissue inhibitor of metalloproteinase 2 and insulin-like growth factor-binding protein 7, New biomarker combination for early recognition of acute kidney injury in cardiac surgery" Zeitschrift fur Herz-, Thorax-und Gefaesschirurgie, Mar. 1, 2017, 31:190-199 (in German, includes English abstract on p. 192; cited by EPO in document D10).

Venugopal et al., "Effect of Remote Ischemic Preconditioning on Acute Kidney Injury in Nondiabetic Patients Undergoing Coronary Artery Bypass Graft Surgery: A Secondary Analysis of 2 Small Randomized Trials," Am J Kidney Dis, Dec. 2010, 56(6-2):1043-1049.

Vijayan et al., "Clinical Use of the Urine Biomarker [TIM P-2] x [IGFBP7]for Acute Kidney Injury Risk Assessment," Am J Kidney Dis, 2016, 68(1):19-28.

Extended European Search Report dated Dec. 3, 2020, in European application (No. 18797960.4).

Official Action dated Dec. 16, 2020, in Chinese patent application (No. 201780045564.9).

Official Action dated Apr. 20, 2021, in European application (No. 17810896.5).

* cited by examiner

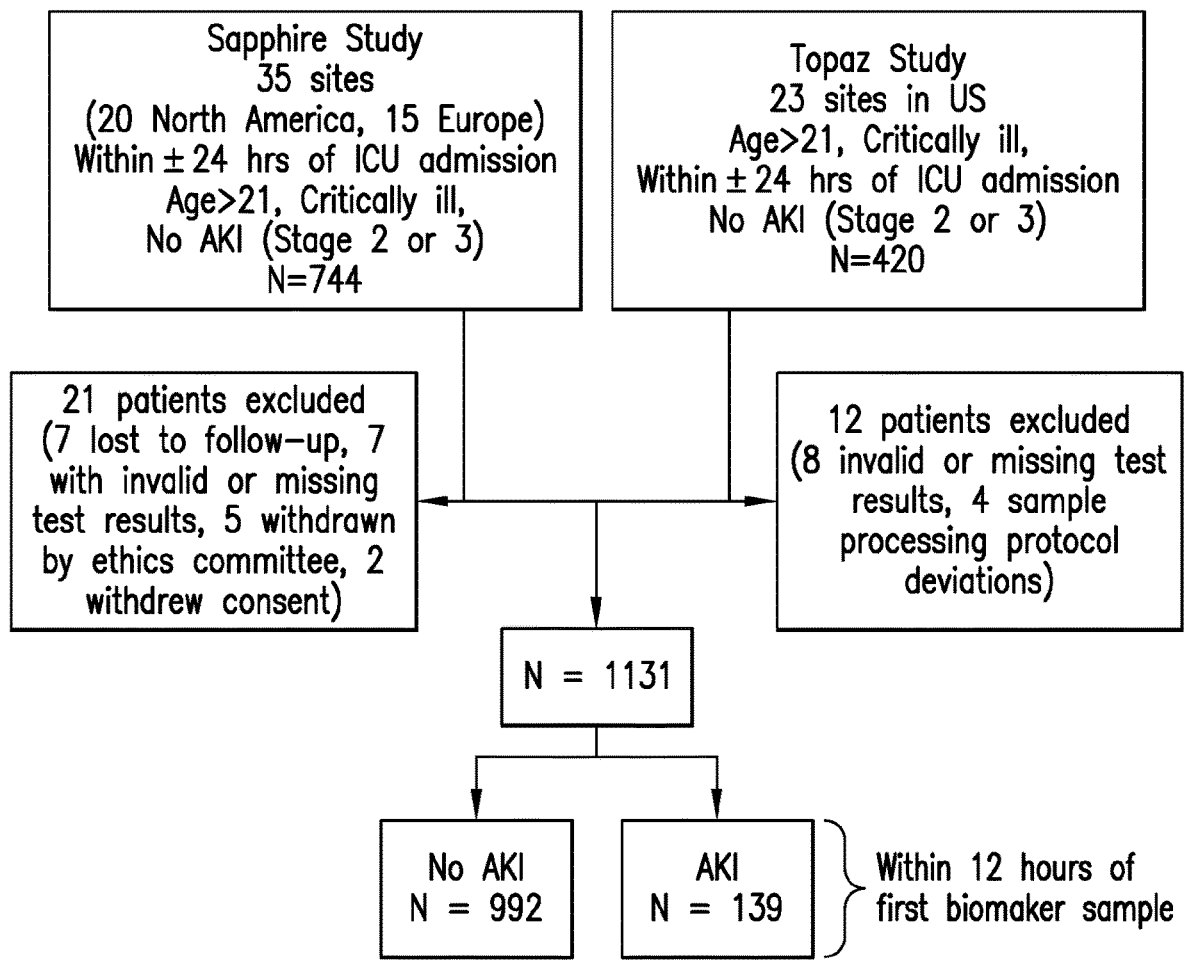

MANAGEMENT OF ACUTE KIDNEY INJURY USING INSULIN-LIKE GROWTH FACTOR-BINDING PROTEIN 7 AND TISSUE INHIBITOR OF METALLOPROTEINASE 2

The present application claims the benefit of U.S. Provisional Patent Application 62/346,381 filed Jun. 6, 2016, which is hereby incorporated by reference in its entirety including all tables, figures and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |

-continued

| Type | Risk Factors |
| --- | --- |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum In an effort to reach consensus on a unified classification system for using serum creatinine to define AKI in clinical trials and in clinical practice, Bellomo et al., Crit Care. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 µmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, Crit. Care Med. 36: S141-45, 2008 and Ricci et al., Kidney Int. 73, 538-546, 2008, each hereby incorporated by reference in its entirety, the RIFLE criteria provide a uniform definition of AKI which has been validated in numerous studies.

More recently, Mehta et al., Crit. Care 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 µmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 µmol/L accompanied by an acute increase of at least 44 µmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

In contrast, chronic kidney disease (CKD) is a different clinical entity characterized by irreversible nephron loss. A progressive decline in renal function is observed over a period of months or years with few, if any, symptoms until the chronic injury is far advanced. CKD is characterized histologically by the concurrent development of glomerulosclerosis and tubulointerstitial fibrosis. Podocyte damage and loss has been identified as a key mechanism, at which a number of glomerular pathomechanisms converge to result in glomerulosclerosis. The mesangial cell is the major matrix forming cell in the glomerulus and is also pivotal to the glomerulosclerotic process, while the activated (alpha-smooth muscle actin-positive) interstitial fibroblast or myofibroblast is central to the development of tubulointerstitial fibrosis. In chronic renal failure, the tubules become scarred causing water loss. In contrast to the oliguria seen in AKI, CKD typically results in polyuria (increased urine volume).

The Merck Manual discusses the need to distinguish between acute renal failure and chronic renal disease, as these are different conditions with different therapies (see, inter alia, page 1846, right hand column, section "Diagnosis", first sentence "the first step is to determine whether the renal failure is acute, chronic or super-imposed on chronic, and Table 222-4 on page 1847 "Classification of Acute Versus Chronic Renal Failure). Recently, a prospective, multicenter investigation in which two novel biomarkers for AKI were identified in a discovery cohort of critically ill adult patients and subsequently validated using a clinical assay and compared to existing markers of AKI in an independent validation cohort of heterogeneous critically ill patients. Urinary insulin-like growth factor binding protein 7 (IGFBP7) and tissue inhibitor of metalloproteinase 2 (TIMP-2) robust markers that have improved performance characteristics when directly compared with existing methods for detecting risk for AKI, but also provide significant additional information over clinical data. It is notable that IGFBP7 and TIMP-2 are each involved with the phenomenon of $G_1$ cell cycle arrest during the very early phases of cell injury, it has been shown that renal tubular cells enter a short period of G1 cell-cycle arrest following injury from experimental sepsis or ischemia. See, e.g., Yang et al., J. Infect. 58:459-464, 2009; Witzgall et al., J. Clin. Invest. 93:2175-2188, 1994.

BRIEF SUMMARY OF THE INVENTION

It is an object of the present invention to provide methods and compositions for identification of subjects at risk of having CKD, and the short term risk of AKI superimposed on CKD.

In a first aspect, the present invention relates to methods for managing a patient not suffering from acute kidney injury (AKI) prior to and following a medical surgical procedure which compromises kidney function. These methods comprise:
calculating a risk score which is a composite of a urinary concentration of IGFBP7 (insulin-like growth factor-binding protein 7) and a urinary concentration of TIMP-2 (tissue inhibitor of metalloproteinase 2) by measuring each of an IGFBP7 concentration and TIMP-2 concentration in a urine sample obtained from the patient immediately prior to performing the medical or surgical procedure and mathematically combining the IGFBP7 and TIMP-2 concentrations to provide the risk score;
comparing the risk score to a risk score threshold value, wherein when the risk score is below the risk score threshold value the patient is determined to be at a higher risk of having CKD as compared to when the risk score is above the risk score threshold value.

If an elevated risk of CKD is identified, the patient may be managed according to clinical practice for the CKD patient. See, e.g., Kidney Intl. 3(1), 1-136, January 2013, which is hereby incorporated by reference. This can include, but is not limited to, assessment of GFR and albuminuria, manage blood pressure to a target, monitoring for acute kidney injury, use of an angiotensin receptor blockers (ARB) or ACE inhibitor (ACE-I).

Alternatively, the risk score threshold value is selected in terms of relative risk. For example, when the risk score is below the risk score threshold value the patient is determined to be at an at least 1.5-fold higher risk of having CKD as compared to when the risk score is above the risk score threshold value. This is not meant to be limiting. Thus, in various embodiments, the increased relative risk may be at least a 2-fold increased risk, at least a 3-fold increased risk, etc.

Various methods may be used to determine risk score thresholds. By way of example, the risk score threshold is selected based on the results of a population study of individuals which includes a individuals having CKD and individuals not having CKD, wherein a urine sample is obtained from each of the individuals, and a risk score is calculated for each of the individuals from the urine sample, and wherein the risk score threshold value is selected to separate the population into a first subpopulation of the individuals with a risk score that is less than the risk score threshold value and a second subpopulation of the individuals with a risk score that is greater than the risk score threshold value, wherein the first subpopulation has an at least 1.5-fold higher risk of having CKD as compared to the second subpopulation.

In certain embodiments, the methods comprise mathematically combining the concentrations comprises multiplying the IGFBP7 concentration or a value obtained therefrom and the TIMP-2 concentration or a value obtained therefrom. For example, the risk score may be expressed mathematically as ([TIMP-2]·[IGFBP7])/1000. In these embodiments, the first risk score threshold value can be about 0.06 and the second risk score threshold value can be about 0.3.

In a related aspect, the present invention relates to methods for identifying and treating a subject as having a frail kidney, wherein the subject is not identified as having an acute kidney injury or chronic kidney disease (CKD). These methods comprise:
calculating a risk score which is a composite of a urinary concentration of IGFBP7 (insulin-like growth factor-binding protein 7) and a urinary concentration of TIMP-2 (tissue inhibitor of metalloproteinase 2) by measuring each of an IGFBP7 concentration and TIMP-2 concentration in a urine sample obtained from the patient and mathematically combining the IGFBP7 and TIMP-2 concentrations to provide the risk score;
comparing the risk score to a risk score threshold value, wherein when the risk score is below the risk score threshold value the patient is determined to be at a higher risk of having a frail kidney as compared to when the risk score is above the risk score threshold value; and
if the risk score is below the threshold value, optionally managing the subject as a CKD patient.

In certain embodiments, the risk score threshold is selected based on the results of a population study of individuals which includes a individuals having CKD and individuals not having CKD, wherein a urine sample is obtained from each of the individuals, and a risk score is calculated for each of the individuals from the urine sample, and wherein the risk score threshold value is selected to separate the population into a first subpopulation of the individuals with a risk score that is less than the risk score threshold value and a second subpopulation of the individuals with a risk score that is greater than the risk score threshold value, wherein the first subpopulation has an at least 1.5-fold higher risk of having CKD as compared to the second subpopulation.

In alternative embodiments, the risk score threshold is selected based on the results of a population study of healthy individuals, wherein a urine sample is obtained from each of the individuals, and a risk score is calculated for each of the individuals from the urine sample, and wherein the risk score threshold value is represented by low risk scores in the population. By way of example, a suitable risk score threshold value may be the upper limit of the lowest 20% of values in the population, lowest 15% of values, lowest 10% of values, lowest 5% of values, etc.

In certain embodiments, mathematically combining the concentrations comprises multiplying the IGFBP7 concentration or a value obtained therefrom and the TIMP-2 concentration or a value obtained therefrom. In preferred embodiments, the risk score is expressed mathematically as ([TIMP-2]·[IGFBP7])/1000, and the risk score threshold value between about 0.12 to about 0.04, preferably between about 0.09 to about 0.04, and is most preferably is about 0.07 or less.

The term "about" as used herein refers to +/−10% of a given value.

In certain embodiments, the urinary concentration of IGFBP7 and the urinary concentration of TIMP-2 are measured using an instrument that receives the urine sample, performs a specific binding assay, and reports the assay result(s) in a form readable by the operator. In one example, the concentrations may be obtained by introducing the urine sample obtained from the patient into an immunoassay instrument; wherein the immunoassay instrument comprises a solid phase, an IGFBP7 antibody immobilized at a first location on the solid phase, and a TIMP-2 antibody immobilized at a second location on the solid phase; wherein the instrument causes the urine sample to contact the first location and the second location; wherein the instrument measures the amount of IGFBP7 which binds to the IGFBP7 antibody immobilized at the first location and determines therefrom the concentration of IGFBP7 in the urine sample; wherein the instrument measures the amount of TIMP-2 which binds to the TIMP-2 antibody immobilized at the second location and determines therefrom the concentration of TIMP-2 in the urine sample; wherein the instrument mathematically combines the concentration of IGFBP7 and the concentration of TIMP-2 in the urine sample into the risk score; and wherein the instrument reports the risk score in a human readable form.

Preferred are sandwich immunoassays. In these embodiments, the urine sample obtained from the patient may be further contacted with a second IGFBP7 antibody conjugated to detectable label and a second TIMP-2 antibody conjugated to detectable label; wherein first sandwich complexes are formed between the IGFBP7 antibody, IGFBP7 present in the urine sample, and the second IGFBP7 antibody; wherein second sandwich complexes are formed between the TIMP-2 antibody, TIMP-2 present in the urine sample, and the second TIMP-2 antibody; wherein the amount of IGFBP7 which binds to the IGFBP7 antibody is determined by the instrument detecting the detectable label bound at the first location; and wherein the amount of TIMP-2 which binds to the TIMP-2 antibody is determined by the instrument detecting the detectable label bound at the second location.

Managing the patient as high risk for future AKI may be performed as described in the KDIGO Clinical Practice Guideline for Acute Kidney Injury, Kidney Intl. 2 (Suppl. 1), March 2012, pp 1-138. In certain embodiments, management can comprise one or more of discontinuing or avoiding one or more nephrotoxic agents, maintaining kidney oxygen perfusion during the surgical procedure, maintaining a protein intake of at least 0.8 g/kg/day, maintaining plasma glucose within the range of 110-149 mg/dL, and performing intravenous administration of isotonic solutions to maintain hemodynamic status. As discussed above, the methods described herein may be used prophylactically in advance of, or as a treatment following, various treatments or conditions that are known to be injurious to the kidney.

Managing the patient for CKD may be performed as described in Kidney Disease: Improving Global Outcomes (KDIGO) CKD Work Group. KDIGO 2012 Clinical Practice Guideline for the Evaluation and Management of Chronic Kidney Disease. *Kidney inter., Suppl.* 2013; 3: 1-150. In certain embodiments, management can comprise one or more of management of blood pressure, renin-angiotensin-aldosterone system ("RAAS") interruption, glycemic control and dietary/lifestyle manipulations which have been examined in the context of delaying progression of CKD; management of anemia in CKD; managing calcium abnormalities associated with CKD; managing metabolic acidosis; and managing AKI risks.

In certain embodiments, the subject is selected for risk stratification based on the subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, tacrolimus, aminoglycosides, foscarnet, ethylene glycol, hemoglobin, myoglobin, ifosfamide, heavy metals, methotrexate, radiopaque contrast agents, or streptozotocin.

Additional clinical indicia of health status, and particularly of renal sufficiency, may be combined with the IGFBP7 and/or TIMP-2 measurements in the methods described herein. Such clinical indicia may include one or more of: a baseline urine output value for the patient, a baseline change in serum creatinine for the patient, demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), other clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with IGFBP7 and/or TIMP-2 assay result(s) are described hereinafter and in Harrison's Principles of Internal Medicine, 17th Ed., McGraw Hill, New York, pages 1741-1830, and Current Medical Diagnosis & Treatment 2008, 47th Ed, McGraw Hill, New York, pages 785-815, each of which are hereby incorporated by reference in their entirety.

As noted above, various methods may be used to evaluate the IGFBP7 and/or TIMP-2 biomarker results. By way of example, a cutoff for a biomarker or a combination of biomarkers may be selected which has been predetermined to divide a relevant population into two or more groups. A first group, often called the "nondiseased" population for convenience, represents those patients which have a high risk of CKD or CKD superimposed with AKI. A second group represents those patients with a risk of CKD or CKD superimposed with AKI is lower as measured by the biomarker result. A relative risk of CKD or CKD superimposed with AKI for the second group is determined relative to the risk in the first group. A relative risk of 1 means there is no difference in risk between the two groups; while a relative risk of >1 means the risk is higher in the second group.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured IGFBP7 and/or TIMP-2 concentrations may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

- an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;
- a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
- a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
- at least about 75% sensitivity, combined with at least about 75% specificity;
- a positive likelihood ratio (calculated as sensitivity/(1-specificity)) of greater than 1, at least about 2, more preferably at least about 3, still more preferably at least about 5, and most preferably at least about 10; or
- a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

BRIEF DESCRIPTION OF THE DRAWINGS

FIG. 1 shows the flow of patient recruitment from both the Sapphire and Topaz studies.

DETAILED DESCRIPTION OF THE INVENTION

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 μmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, chronic kidney disease or "CKD" is CKD is defined as abnormalities of kidney structure or function, present for >3 months, with implications for health. Approximately 11% of U.S. adults reportedly have CKD, many of whom are elderly. The condition is usually asymptomatic until its advanced stages.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components. A body fluid sample is obtained "immediately prior to" a procedure if it is obtained within 72 hours of initiating the procedure, and preferably within 48 hours, 24 hours, 18 hours, 12 hours, or 6 hours thereof.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

IGFBP7 and TIMP-2 Assays

In general, immunoassays are specific binding assay that involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), lateral flow assays, competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Such assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of IGFBP7 and/or TIMP-2. The kit comprises reagents for the analysis of at least one test sample which comprise at least one antibody that bind each biomarker being assayed. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1—specificity, the ROC graph is sometimes called the sensitivity vs (1—specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined in the methods of the present invention are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 26 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant. 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

The distinction between prerenal AKI and intrinsic AKI is an important clinical assessment that directs the therapeutic intervention(s). Patients who are prerenal need therapies directed at hemodynamics to improve renal blood flow. These therapies are often involve inotropes, intravenous fluids and/or vasopressors. Each of these interventions have potential side effects (e.g. arrhythmias, volume overload, vasoconstriction) and would not be advisable to implement these therapies if they are not destined to improve renal function. Thus, the distinction between prerenal AKI and intrinsic AKI helps determine the therapy which should be prescribed. If prerenal AKI is not present, therapy is directed at mitigating AKI and providing supportive care.

Prerenal acute renal failure occurs when a sudden reduction in blood flow to the kidney camera (renal hypoperfusion) causes a loss of kidney function. Causes can include low blood volume, low blood pressure, shunting of blood from the kidney, heart failure, and local changes to the blood vessels supplying the kidney. In prerenal acute renal failure, there is nothing wrong with the kidney itself. Treatment focuses on correcting the cause of the prerenal acute renal failure.

In prerenal AKI without fluid overload, administration of intravenous fluids is typically the first step to improve renal function. This is particularly used in patients in whom prerenal AKI develops as the result of intravascular volume depletion in order to restore normal circulating blood volume. Volume status may be monitored to avoid over-or under-replacement of fluid as described herein. Fluids with colloidal particles such as albumin may be preferred over simple saline infusion. In a prerenal condition wherein the forward flow is compromised, drugs directed at augmenting cardiac output are typically employed.

In patients with congestive heart failure in whom AKI has developed as a result of excessive diuresis, withholding of diuretics and cautious volume replacement may be sufficient to restore kidney function. Inotropes such as norepinephrine and dobutamine may be given to improve cardiac output and hence renal perfusion.

Hospitalized fluid overload patients are typically treated with fluid restriction, IV diuretics, inotropes (e.g., milrinone or dobutamine) and combination therapies. The loop diuretic furosemide is the most frequently prescribed diuretic for treatment of volume overload in HF. Initial oral doses of 20 to 40 mg once a day should be administered to patients with dyspnea on exertion and signs of volume overload who do not have indications for acute hospitalization. Severe overload and pulmonary edema are indications for hospitalization and intravenous furosemide. Some patients with mild HF can be treated effectively with thiazide diuretics. Those who have persistent volume overload on a thiazide diuretic should be switched to an oral loop diuretic. In patients with severe kidney injury, diuretics may not result in significant diuresis. Ultrafiltration, also called aquapheresis, may be used to treat fluid overload in such cases.

In contrast to prerenal AKI, the main goal of treatment of acute tubular necrosis (ATN) is to prevent further injury to the kidney. Ischemic ATN can be caused when the kidneys are not sufficiently perfused for a long period of time (e.g. due to renal artery stenosis) or by shock. Sepsis causes 30% to 70% of deaths in patients with ATN; therefore, avoidance of intravenous lines, bladder catheters, and respirators is recommended. Because septic patients are vasodilated, large volumes of administered fluid accumulate in the lung interstitium of these patients. Extracellular fluid volume should be assessed promptly, and repletion of any deficit should be initiated promptly. Hemodynamic status should be modified by appropriate fluid therapy, giving vasopressors and/or inotropes and treating any underlying sepsis. All possible nephrotoxic drugs should be stopped. In addition, doses of all medications that are eliminated by the kidney should be adjusted.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Study Design and Participants

A secondary analysis of data collected from two multi-center clinical trials used to validate [TIMP2]·[IGFBP7] in AKI, the "Sapphire" and "Topaz" studies, was conducted. The Sapphire study enrolled 744 critically ill adult (>21 years) patients who were at risk for development of AKI. In the Topaz study, 420 critically ill adult patients were enrolled, with similar inclusion/exclusion criteria to the Sapphire study. Specifically, subjects in both studies were required to have evidence of significant pulmonary (respiratory SOFA score >2) or cardiovascular (cardiac SOFA score >1) dysfunction, and could not yet have met criteria for moderate-severe AKI (KDIGO stage 2 or 3). Patient recruitment occurred within 24 hours of intensive care unit (ICU) admission. More detailed descriptions of both studies have previously been published. Both the Sapphire and Topaz studies were approved by the Western Institutional Review Board (Olympia, Wash., USA) as well as individual site investigational review boards if required, and written informed consent was obtained from all subjects (or their legally-authorized representatives).

Examples 2: Procedures

Clinical data collection included patient demographics, reason for ICU admission, APACHE III score variables, hourly urine output and laboratory testing results. Comorbid conditions were determined based on review of available medical records and based on diagnostic codes. Estimated GFR was determined using the CKD-EPI equation; patients with missing or unknown race were considered not to be black. Each site extracted data from clinical sources and input the data into an online electronic case-report form in a de-identified password-protected dataset. Study data was stored at an independent server site (Medidata Solutions, New York, N.Y.).

The primary outcome was moderate to severe AKI as defined by KDIGO criteria (KDIGO Clinical Practice Guideline for Acute Kidney Injury, 2012) for stage 2 or 3 AKI developing within 12 hours of enrollment. In the TOPAZ study, final determination of AKI was adjudicated by an expert panel of 3 independent nephrologists who were blinded to biomarker results.

Example 3: Analysis

Urine and blood samples were collected and processed using standard methods. Sample supernatants were frozen within 2 hours of collection and stored at −70° C. before batched transport to a central lab for analysis. Samples were thawed immediately before analysis. Testing for [TIMP2]·[IGFBP7] was performed using a clinical immunoassay (NEPHROCHECK Test and ASTUTE140 Meter; Astute Medical Inc., San Diego, Calif.) and lab technicians performing the testing were blinded to patient outcomes. For subjects recruited in the Sapphire study, [TIMP2]·[IGFBP7] testing was performed at Astute Medical Inc. laboratories; in the Topaz study, testing was performed in triplicate at 3 independent laboratories (University of California at San Diego, University of Louisville, and ARUP Laboratories in Salt Lake City). Test results for [TIMP2]·[IGFBP7] are uniformly reported in units of (ng/ml)2/1000 throughout the text.

Continuous variables were compared between AKI groups using Wilcoxon rank sum test or t-test. Categorical variables were compared between AKI groups using Chi-square test. To assess the effect of comorbidity on levels of [TIMP2]·[IGFBP7], we performed multiple linear regression analysis for each comorbidity where the response variable is rank transformed [TIMP2]·[IGFBP7] and the explanatory variables are AKI status, comorbidity status, and the interaction between them. AUC calculation and testing for difference in two AUCs were based on the Delong method, using R package "pROC"0.12 When necessary P values were adjusted for multiple testing by Benjamini-Hochberg method. A multivariate logistic regression model was constructed to predict the primary outcome of AKI accounting for comorbid conditions. Backward selection was used to eliminate variables with p<0.10 and arrive at the final model. Statistical analyses were performed using R version 3.1.0. (R Foundation, www.r-project.org/) and SAS 9.3 (SAS Institute, Cary, N.C.).

Example 4: Results

FIG. 1 shows the flow of patient recruitment from both the Sapphire and Topaz studies. A total of 1164 patients were recruited; in the Sapphire study, 21 (2.8%) patients were excluded after enrollment, while 12 (2.9%) patients were excluded in the Topaz study. Patient characteristics were similar between the two studies. The final cohort consisted of 1131 patients, of whom 139 (12.3%) developed moderate-severe AKI (KDIGO stage 2 or 3). 5 For simplicity, throughout the example AKI will refer to KDIGO stage 2 or 3 AKI, while no AKI will indicate either no AKI or stage 1 AKI.

Patient characteristics stratified by AKI status are shown in Table 1. A greater percentage of patients who developed AKI had pre-existing diabetes and hypertension compared to patients without AKI. The percentage of patients with underlying CKD was similar between AKI groups, but median enrollment serum creatinine was higher in patients who developed AKI.

Patients characteristics, stratified by acute kidney injury status. Categorical variables are shown as N (%) and numerical as mean (standard deviation) or median (interquartile range).

|  | No AKI or Stage 1 | AKI Stage 2 or 3 | P-value |
|---|---|---|---|
| All patients | 992 | 139 | |
| Male | 589 (59%) | 74 (53%) | 0.169 |
| Age, Years | 62 (16) | 65 (15) | 0.081 |
| Body Mass Index, kg/m$^2$ | 27 (24-32) | 31 (26-38) | <0.001 |
| Race | | | 0.948 |
| Black | 127 (13%) | 16 (12%) | |
| White | 794 (80%) | 113 (81%) | |
| Other/Unknown | 70 (7%) | 10 (7%) | |
| Medical History | | | |
| Chronic Kidney Disease | 84 (8%) | 13 (9%) | 0.746 |
| Diabetes Mellitus | 274 (28%) | 52 (37%) | 0.021 |
| Congestive Heart Failure | 174 (18%) | 32 (23%) | 0.127 |
| Coronary Artery Disease | 296 (30%) | 40 (29%) | 0.843 |
| Hypertension | 599 (60%) | 101 (73%) | 0.005 |
| Chronic Obstructive Pulmonary Disease | 213 (21%) | 23 (17%) | 0.220 |
| Admitted to ICU from | | | 0.244 |
| ED | 380 (38%) | 62 (45%) | |
| Floor | 175 (18%) | 18 (13%) | |
| OR | 275 (28%) | 30 (22%) | |
| Other Hospital | 140 (14%) | 25 (18%) | |
| Other ICU | 10 (1%) | 1 (1%) | |
| Unknown | 12 (1%) | 3 (2%) | |
| Reason for ICU Admission | | | |
| Respiratory | 447 (45%) | 67 (48%) | 0.525 |
| Surgery | 340 (34%) | 35 (25%) | 0.034 |
| Cardiovascular | 345 (35%) | 58 (42%) | 0.130 |
| Sepsis | 192 (19%) | 40 (29%) | 0.013 |
| Neurological | 112 (11%) | 10 (7%) | 0.188 |
| Trauma | 89 (9%) | 10 (7%) | 0.630 |
| Other | 207 (21%) | 40 (29%) | 0.038 |
| Time from ICU admission to biomarker sample collection, Hours | 16 (7-20) | 16 (11-20) | 0.427 |
| Non-Renal Apache III | 57 (43-78) | 69 (50-87) | <0.001 |
| Enrollment eGFR*, mL/min/1.73 m$^2$ | 82 (55-101) | 52 (31-84) | <0.001 |
| Enrollment serum creatinine**, mg/dL | 0.9 (0.7-1.2) | 1.3 (0.9-1.8) | <0.001 |
| 6-hour cumulative urine output at enrollment†, mL | 424 (280-705) | 185 (115-303) | <0.001 |
| Radiocontrast agents‡ | 354 (36%) | 47 (34%) | 0.706 |
| Blood transfusions§ | | | |
| PRBC | 283 (29%) | 32 (23%) | 0.190 |
| Platelets | 98 (10%) | 19 (14%) | 0.180 |
| Fresh Frozen Plasma | 139 (14%) | 25 (18%) | 0.246 |
| Albumin | 143 (14%) | 25 (18%) | 0.255 |
| Cryoprecipitate | 24 (2%) | 2 (1%) | 0.761 |

AKI: acute kidney injury, defined by KDIGO criteria;
ED: emergency department;
OR: operating room;
ICU: intensive care unit;
eGFR: estimated glomerular filtration rate
*Calculated from enrollment serum creatinine using the Chronic Kidney Disease Epidemiology Collaboration (CKD-EPI) equation.
**Value from medical record closest to time of enrollment.
†15% of No AKI or Stage 1 and 12% of AKI Stage 2 or 3 did not have urine output data for 6 hours prior to enrollment.
‡Number of patients receiving IV or IA contrast administered within 5 days prior to and including the day of enrollment
§Number of patients receiving blood products within 5 days prior to and including the day of enrollment In the overall cohort, median [TIMP2]·[IGFBP7] was significantly higher in AKI patients compared to non-AKI patients (1.5 [IQR 0.6-2.8] vs. 0.3 [IQR 0.1-0.7], p<0.001). These values were consistent across a variety of comorbid states, and remained statistically different between AKI and non-AKI patients.

In the cohort of 97 patients with CKD, the AUC for [TIMP2]·[IGFBP7] prediction of moderate-severe AKI was 0.91 (95% CI 0.85-0.97). The relative risk for AKI with a [TIMP2]·[IGFBP7] value above the previously validated cut-off of 0.3 was 32.4 (95% CI 3.7-284.8). In non-AKI patients, the presence of CKD was associated with lower [TIMP2]·[IGFBP7]. The AUC (95% CI) of [TIMP2]·[IGFBP7] for discrimination of CKD from non-CKD in non-AKI patients was 0.60 (0.54-0.66), p=0.001. [TIMP2]·[IGFBP7] in patients without moderate-severe AKI by CKD status.

| | | [TIMP2]•[IGFBP7] | | | |
|---|---|---|---|---|---|
| CKD Status | Number of Patients | Median | 25$^{th}$ percentile | 75$^{th}$ percentile | p-value* |
| Yes | 84 | 0.22 | 0.08 | 0.44 | 0.002 |
| No | 908 | 0.31 | 0.13 | 0.74 | |

*Wilcoxon rank sum test

The percentage of patients with CKD decreased from 12.1% to 5.6% across [TIMP2]·[IGFBP7] quartiles, p=0.006 for Cochran-Armitage trend test. The odds ratio (OR) for CKD was 2.3, p=0.013, for the first quartile relative to the fourth quartile.

Percentage and odds ratio for CKD by [TIMP2]·[IGFBP7] quartile in patients without moderate-severe AKI.

| Quartile | [TIMP-2]•[IGFBP7] | Number without CKD | Number with CKD | Percent with CKD | OR relative to Q4 | 95% Confidence Interval | p |
|---|---|---|---|---|---|---|---|
| 1 | <=0.13 | 218 | 30 | 12.1% | 2.30 | 1.19-4.45 | 0.013 |
| 2 | >0.13 to <=0.3 | 226 | 23 | 9.2% | 1.70 | 0.85-3.39 | 0.131 |
| 3 | >0.30 to <=0.73 | 230 | 17 | 6.9% | 1.24 | 0.60-2.56 | 0.571 |
| 4 | >0.73 | 234 | 14 | 5.6% | 1 | — | — |

Example 5: [TIMP2]·[IGFBP7] in Healthy Donors

Urine sample were collected from 378 healthy donors and tested for [TIMP2]·[IGFBP7] as described in Chindarkar, N S, et al. "[IGFBP7]·[TIMP2] in apparently healthy subjects and chronic comorbid subjects without AKI", Clin Chim Acta. 2016 Jan. 15; 452:32-7. [TIMP2]·[IGFBP7] values corresponding to percentiles ranging from the 2.5th to 97.5th percentile in 2.5% increments are shown in the table below. The reportable range of the [TIMP2]·[IGFBP7] assay is from 0.04 to 10.00 $(ng/mL)^2/1000$.

| Percentile | [TIMP-2]•[IGFBP7], $(ng/mL)^2/1000$ |
|---|---|
| 2.5% | 0.04 |
| 5.0% | 0.05 |
| 7.5% | 0.06 |
| 10.0% | 0.07 |
| 12.5% | 0.08 |
| 15.0% | 0.09 |
| 17.5% | 0.11 |
| 20.0% | 0.12 |
| 22.5% | 0.13 |
| 25.0% | 0.14 |
| 27.5% | 0.16 |
| 30.0% | 0.17 |
| 32.5% | 0.19 |
| 35.0% | 0.21 |
| 37.5% | 0.22 |
| 40.0% | 0.24 |
| 42.5% | 0.26 |
| 45.0% | 0.28 |
| 47.5% | 0.30 |
| 50.0% | 0.32 |
| 52.5% | 0.36 |
| 55.0% | 0.40 |
| 57.5% | 0.43 |
| 60.0% | 0.45 |
| 62.5% | 0.47 |
| 65.0% | 0.51 |
| 67.5% | 0.55 |
| 70.0% | 0.59 |
| 72.5% | 0.66 |
| 75.0% | 0.74 |
| 77.5% | 0.80 |
| 80.0% | 0.89 |
| 82.5% | 0.95 |
| 85.0% | 1.06 |
| 87.5% | 1.18 |
| 90.0% | 1.29 |
| 92.5% | 1.47 |
| 95.0% | 1.85 |
| 97.5% | 2.25 |

Patients in the lowest percentiles of [TIMP2]·[IGFBP7] values indicate a potential for cryptic CKD existing in these patients, a state referred to herein as having a "frail kidney." While not wishing to be bound by any theory, patients with low [TIMP2]·[IGFBP7] values may be unable to respond effectively to kidney stress, thus resulting in an increased risk of damage from an insult. Treating such individuals (e.g., those in the lowest 10% of values) as if they suffer from CKD can avoid such damage to these individuals.

Example 6: Pre-Operative Evaluation of Frail Kidney

The following is an example of a pre-operative evaluation in a stable (not acutely ill) patient. For a patient who has not been diagnosed with CKD and is undergoing a procedure with a high (>5%) risk of acute kidney injury (e.g. coronary artery bypass).

| [TIMP2]•[IGFBP7] | Interpretation | Action |
|---|---|---|
| <0.07 | Frail kidney | Treat as CKD |
| 0.07-0.5 | Normal risk | Treat as per normal risk |
| >0.5 | Possible AKI | Review exposures monitor for 48 h |

For those with frail kidney, the following actions should be considered:
  Consider alternatives to surgery as consistent with patient goals and preferences
  Preoperative nephrology consultation
  Preform remote ischemic preconditioning
  Perform surgery using off-pump technique
  Start an ACE inhibitor and recheck test in 3-4 weeks Example 7: Routine Evaluation of Frail Kidney The following is an example of a routine health screen (e.g. annual physical).

| Test result | Interpretation | Action |
|---|---|---|
| <0.07 | Frail kidney | Treat as CKD |
| 0.07-0.5 | Normal risk | None |
| >0.5 | Possible AKI | Review for kidney stress** |

For those with frail kidney, the following actions should be considered:
  Test urine for albumin and measure serum creatinine every 3-6 months
  Screen for hypertension, diabetes - follow management guidelines for CKD
  Avoid nephrotoxic medications (e.g. NSAIDS); switch to less nephrotoxic meds
  Start an ACE inhibitor and recheck test in 3-4 months
**The following actions could be considered:
  Review medications for potential source of stress - discontinue offending agent
  Review lifestyle (e.g. extreme exercise) and modify accordingly While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of treating frail kidney in a subject, the method comprising administering an angiotensin receptor blocker (ARB), administering an ACE inhibitor (ACE-I), administering an agent for interrupting a renin-angiotensin-aldosterone system (RAAS), performing remote ischemic preconditioning, performing surgery using an off-pump technique, or withdrawing delivery of compounds that are known to be damaging to the kidney, to a subject having a frail kidney risk score below a predetermined threshold value, wherein the risk score is based on a concentration of IGFBP7 (insulin-like growth factor-binding protein 7) and a concentration of TIMP-2 (tissue inhibitor of metalloproteinase 2) in a urine sample obtained from the subject, wherein the risk score is based on the formula ([TIMP-2]×[IGFBP7])/1000 and is at or below about 0.07, and wherein the [TIMP-2] and [IGFBP7] are in units of ng/ml.

2. The method of claim 1, wherein the risk score is lower than a threshold value selected based on the results of a population study of healthy individuals, wherein the threshold value is the risk score value for the lowest tenth percentile of risk scores in the population.

3. The method of claim 1, wherein the subject is expected to undergo major vascular surgery, coronary artery bypass surgery, or cardiac surgery.

4. A method of claim 2, wherein the threshold value is about 0.07.

5. The method of claim 4, wherein the subject is expected to undergo major vascular surgery, coronary artery bypass surgery, or cardiac surgery.

* * * * *

UNITED STATES PATENT AND TRADEMARK OFFICE
CERTIFICATE OF CORRECTION

PATENT NO. : 11,243,217 B2
APPLICATION NO. : 16/307366
DATED : February 8, 2022
INVENTOR(S) : Paul McPherson et al.

Page 1 of 1

It is certified that error appears in the above-identified patent and that said Letters Patent is hereby corrected as shown below:

In the Claims

Claim 2, Column 28, Line 24, the text "than a threshold value selected based on the results of a" should be changed to --than a threshold value selected based on results of a--

Claim 2, Column 28, Line 26, the text "wherein the threshold value is the risk score value for the" should be changed to --wherein the threshold value is a risk score for the--

Claim 4, Column 28, Line 31, the text "A method of claim 2, wherein the threshold value is" should be changed to --The method of claim 2, wherein the threshold value is--

Signed and Sealed this
Thirteenth Day of September, 2022

Katherine Kelly Vidal
*Director of the United States Patent and Trademark Office*